(12) United States Patent
Wolk et al.

(10) Patent No.: US 6,620,625 B2
(45) Date of Patent: Sep. 16, 2003

(54) ULTRA HIGH THROUGHPUT SAMPLING AND ANALYSIS SYSTEMS AND METHODS

(75) Inventors: Jeffrey A. Wolk, Half Moon Bay, CA (US); Sherri Ann Biondi, Menlo Park, CA (US); J. Wallace Parce, Palo Alto, CA (US); Morten J. Jensen, San Francisco, CA (US); Anne R. Kopf-Sill, Portola Valley, CA (US)

(73) Assignee: Caliper Technologies Corp., Mountain View, CA (US)

( * ) Notice: Subject to any disclaimer, the term of this patent is extended or adjusted under 35 U.S.C. 154(b) by 240 days.

(21) Appl. No.: 09/750,450

(22) Filed: Dec. 28, 2000

(65) Prior Publication Data

US 2001/0049148 A1 Dec. 6, 2001

Related U.S. Application Data

(60) Provisional application No. 60/196,468, filed on Apr. 11, 2000, and provisional application No. 60/174,902, filed on Jan. 6, 2000.

(51) Int. Cl.[7] ............... G01N 1/00; G01N 21/00; G01N 30/02; G01N 30/96; B01L 3/02; B01D 15/00; B01D 15/08; B01D 57/02
(52) U.S. Cl. ............ 436/180; 436/174; 422/100; 422/68.1; 422/63; 422/69; 422/70; 210/656; 210/198.2; 204/451
(58) Field of Search ............ 422/99–101, 56–57, 422/61, 63, 69, 68.1, 70; 436/174, 180; 210/656, 500, 198.2, 199; 204/451

(56) References Cited

U.S. PATENT DOCUMENTS

| | | |
|---|---|---|
| 4,077,845 A | 3/1978 | Johnson |
| 4,452,903 A * | 6/1984 | Lee et al. ............... 436/540 |
| 5,126,022 A | 6/1992 | Soane et al. |
| 5,188,963 A | 2/1993 | Stapleton |
| 5,302,264 A | 4/1994 | Welch et al. |
| 5,443,791 A | 8/1995 | Cathcart et al. |

(List continued on next page.)

FOREIGN PATENT DOCUMENTS

| | | |
|---|---|---|
| DE | 4105107 | 9/1991 |
| EP | 0107631 | 5/1984 |
| EP | 0616218 | 9/1994 |
| EP | 0815 940 | 1/1998 |
| JP | 4-160356 | 6/1992 |
| WO | WO 96/29595 | 9/1996 |
| WO | WO 98/45481 | 10/1998 |

OTHER PUBLICATIONS

BAO, et al., "Ultramicro enzyme assays in a capillary electrophoretic system," *J. Chrom.* (1992) 608:217–224.

Manz, A. et al., "Miniaturized total chemical analysis systems: a novel concept for chemical sensing," *Sensors & Actuators* (1990) B1:244–248.

*Primary Examiner*—Jill Warden
*Assistant Examiner*—Brian R. Gordon
(74) *Attorney, Agent, or Firm*—Gulshan H. Shaver; Matthew B. Murphy; Andrew L. Filler

(57) ABSTRACT

Ultra-high throughput systems and methods are used for sampling large numbers of different materials from surfaces of substantially planar library storage components. The systems and methods typically employ: microfluidic devices having integrated capillary elements for carrying out the analysis of the sampled materials; library storage components, e.g., planar solid substrates, capable of retaining thousands, tens of thousands and hundreds of thousands of different materials in small areas; sensing systems for allowing rapid and accurate sampling of the materials by the microfluidic devices, and associated instrumentation for control and analysis of the overall operation of these systems.

51 Claims, 20 Drawing Sheets

U.S. PATENT DOCUMENTS

| | | |
|---|---|---|
| 5,474,796 A | 12/1995 | Brennan |
| 5,560,811 A | 10/1996 | Briggs et al. |
| 5,593,838 A | 1/1997 | Zanzucchi et al. |
| 5,677,197 A * | 10/1997 | Gordon et al. .............. 436/518 |
| 5,779,868 A | 7/1998 | Parce et al. |
| 5,876,675 A * | 3/1999 | Kennedy ..................... 422/99 |
| 5,880,071 A | 3/1999 | Parce et al. |
| 5,890,745 A | 4/1999 | Kovacs |
| 5,922,534 A * | 7/1999 | Lichtenwalter ................ 435/6 |
| 5,942,443 A | 8/1999 | Parce et al. |
| 5,958,203 A | 9/1999 | Parce et al. |
| 5,972,187 A | 10/1999 | Parce et al. |
| 5,994,142 A | 11/1999 | Yamasaki et al. |
| 6,042,709 A | 3/2000 | Parce et al. |
| 6,046,056 A | 4/2000 | Parce et al. |
| 6,086,740 A | 7/2000 | Kennedy |
| 6,103,199 A | 8/2000 | Bjornson et al. |
| 6,132,685 A * | 10/2000 | Kercso et al. .............. 422/104 |
| 6,149,787 A * | 11/2000 | Chow et al. ................. 204/451 |
| 6,235,471 B1 * | 5/2001 | Knapp et al. ................... 435/6 |
| 6,265,176 B1 * | 7/2001 | Lin et al. .................... 435/7.92 |
| 6,274,089 B1 * | 8/2001 | Chow et al. ................. 422/101 |
| 6,306,590 B1 * | 10/2001 | Mehta et al. ................... 435/6 |
| 6,306,659 B1 * | 10/2001 | Parce et al. ................... 436/47 |
| 6,383,452 B1 * | 5/2002 | Miyake et al. ................. 422/63 |
| 6,413,782 B1 * | 7/2002 | Parce et al. ................. 436/514 |
| 6,458,547 B1 * | 10/2002 | Bryan et al. ................. 435/7.1 |
| 6,465,190 B1 * | 10/2002 | Hirota et al. ................... 435/6 |
| 2002/0015667 A1 * | 2/2002 | Chow ........................ 422/100 |
| 2002/0123133 A1 * | 9/2002 | Mehta et al. ............. 435/287.2 |
| 2002/0146834 A1 * | 10/2002 | Meron et al. ................. 436/66 |
| 2002/0151040 A1 * | 10/2002 | O'Keefe et al .......... 435/287.2 |

* cited by examiner

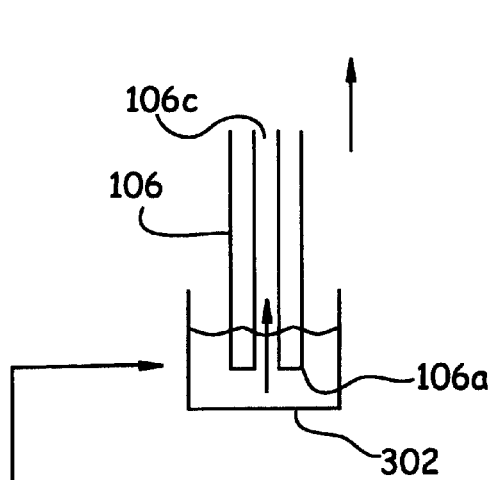
Figure 3A
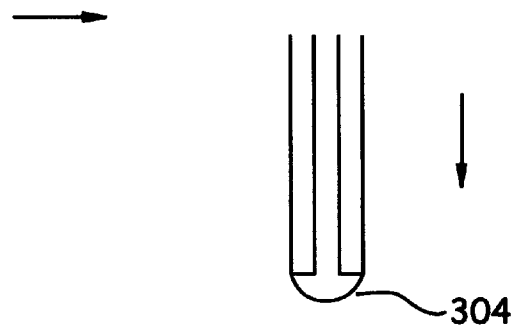
Figure 3B
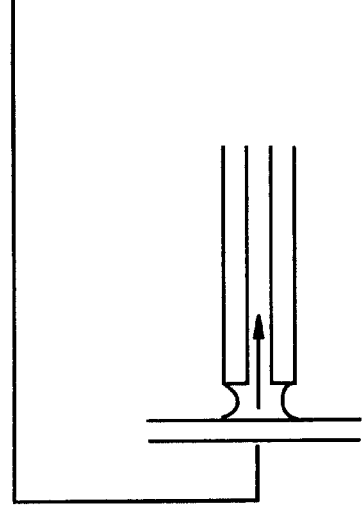
Figure 3D
Figure 3C

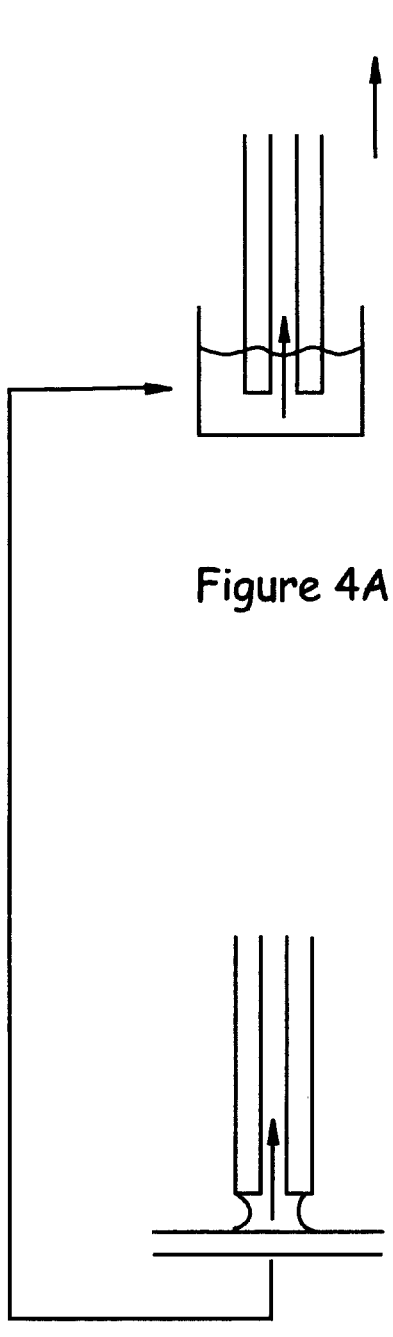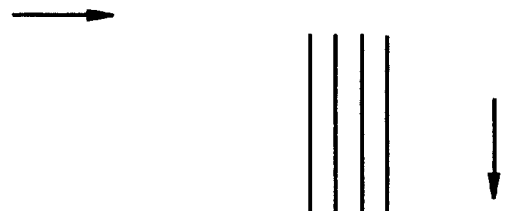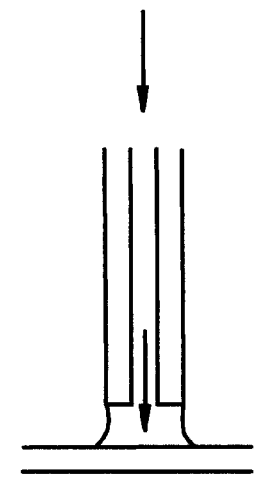
Figure 4A
Figure 4B
Figure 4D
Figure 4C

ULTRA HIGH THROUGHPUT SAMPLING AND ANALYSIS SYSTEMS AND METHODS

CROSS-REFERENCE TO RELATED APPLICATIONS

This application claims priority to Provisional U.S. Patent Application Nos. 60/174,902, filed Jan. 6, 2000, and 60/196,468, filed Apr. 11, 2000, each of which is hereby incorporated herein by reference in its entirety for all purposes.

STATEMENT OF GOVERNMENT RIGHTS

The present invention was made with government finding from the United States National Institute of Standards and Technology (NIST), through the Advanced Technology Program (ATP) under Grant No. 70NANB8H4000, and the United States government has certain rights in the invention.

BACKGROUND OF THE INVENTION

The science of drug discovery has greatly benefited in recent years from dramatic advances made in scientific research and development. For example, on one end of the drug discovery spectrum, the concerted international effort to sequence the human genome has led to the discovery of large numbers of genes and gene products that are potential targets for pharmaceutical agents in the treatment of disease. On the other side of the equation, numerous approaches to combinatorial chemical synthesis have led to the generation of extremely large numbers of different chemical compounds that can be screened for effects on those targets.

Linking the two technologies are a number of advances in technology for screening the large libraries of compounds against large collections of targets. For example, large automated robotic systems have been developed to sample and mix reagents from libraries in multiwell plate formats, performing thousands of different screening reactions in a single day. These systems employ a brute force approach to screening potential pharmaceutical compounds by automating the fluid handling components of the assay process. While these systems are widely used, they provide only a first incremental increase in efficiency over the lone experimenter working at his or her bench. Further, given the ever-expanding numbers of screening assays that are required, it has not taken long for this incremental increase in efficiency to be surpassed by the screening demand.

Microfluidic technology is one of the most recent technologies to be applied in screening pharmaceutical libraries (see, e.g., U.S. Pat. No. 5,942,443). These microfluidic technologies provide benefits in terms of reagent consumption, speed, reproducibility and automatability. Specifically, when performed in the microscale format in fluid volumes on the order of nanoliters or less, reagents mix more quickly, and assays require much smaller quantities of expensive reagents. Further, the integrated nature of microfluidic systems allows for precise computer control of material flow, mixing, data acquisition and analysis allowing for ease of use and improved reproducibility.

Microfluidic systems have also been developed to interface with the traditional library storage format, namely the multiwell plate. In particular, pipettor chips have been developed that include an external sample accessing capillary, see, e.g., U.S. Pat. No. 5,779,868. While such systems provide the advantages of smaller reagent requirements in screening, conventional library storage systems still utilize large reagent volumes, effectively eliminating some of the advantages otherwise provided by microfluidic technology.

While all of the foregoing advances in screening technology have provided significant benefits to the pharmaceutical industry, it would generally be desirable to be able to take advantage of all of the advantages of microfluidic technology in terms of the reagent storage and accessibility. The present invention meets these and a variety of other needs.

SUMMARY OF THE INVENTION

The present invention is generally directed to improved methods, devices and systems for use in high-throughput and even ultra high-throughput assays. Generally, the methods, devices and systems take advantage of novel automation, miniaturization and integration techniques to achieve these goals.

For example, in a first aspect, the present invention provides a method of sampling compounds into a microfluidic channel. In these methods, a plurality of different compounds are provided reversibly immobilized on a first surface of a substrate. A capillary element is also provided having a capillary channel disposed therethrough, where the capillary element has at least one open end, and a volume of solubilizing fluid present at the open end of the capillary element. In accordance with these methods, the solubilizing fluid at the open end of the capillary element is moved into contact with a first compound on the surface of the substrate by sensing when the solubilizing fluid contacts the surface of the substrate. The solubilizing fluid dissolves at least a portion of the first compound, and at least a portion of the dissolved first compound is drawn into the capillary element.

In another aspect, the present invention provides methods of sampling compounds into a microfluidic channel, which, in addition to providing the compounds reversibly immobilized on a substrate, and a capillary, as above, also comprises a drop of solubilizing fluid suspended from the open end of the capillary. The drop of solubilizing fluid suspended from the open end of the capillary element is moved relative to the substrate to place the drop into contact with a first compound immobilized on the first surface of the substrate. At least a portion of the compound solubilized by the drop of solubilizing fluid is then drawn into the microfluidic channel within the capillary element. These steps may be repeated multiple times with respect to one or multiple compounds on the substrate surface.

The present invention also generally provides devices and systems for carrying out the methods described herein or methods similar thereto. For example, in one aspect, the present invention provides systems for analyzing a plurality of different sample materials. The systems typically comprise a microfluidic element comprising a capillary element having at least a first microfluidic channel disposed therethrough, the capillary element having at least one open end The system also typically includes a sample substrate comprising a plurality of different sample materials reversibly immobilized thereon, each different sample being immobilized in a different discrete region of the first surface. A translation system is provided attached to at least one of the substrate or the microfluidic element, for moving either the microfluidic element relative to the substrate surface or vice versa. The system provides for a sensing system for sensing when a volume of fluid at the open end of the capillary element contacts the first surface of the substrate.

BRIEF DESCRIPTION OF THE DRAWINGS

FIG. 3 illustrates one aspect of the operation of the sampling systems of the present invention using a hanging drop of fluid on the end of a capillary element to resolubilize sample material on a substrate surface.

FIG. 4 illustrates an alternate aspect of the operation of the sampling systems of the present invention using an expelled fluid volume to resolubilize sample material on the sample substrate.

DETAILED DESCRIPTION OF THE INVENTION

I. General System Description

Figure 1:
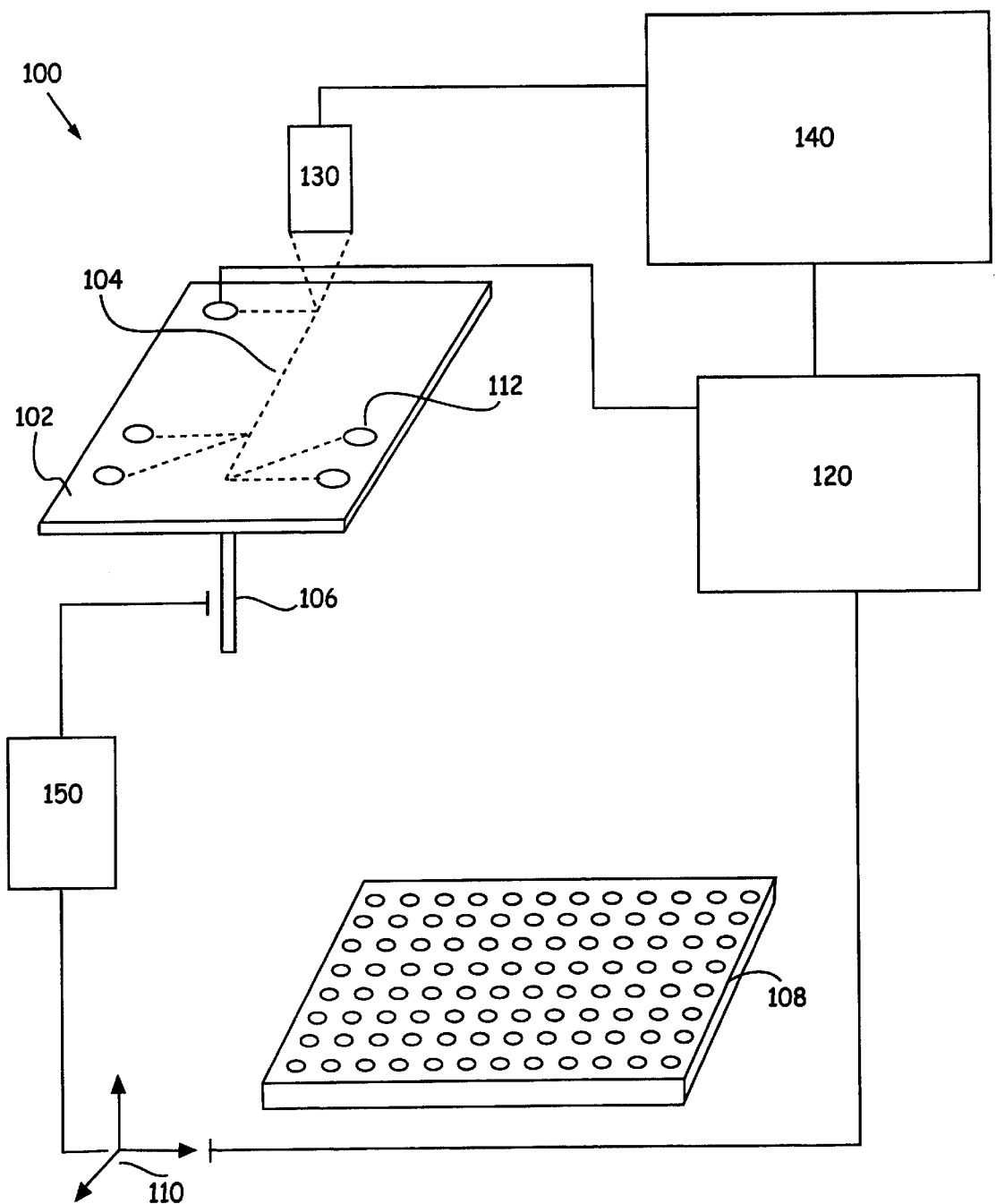
FIG. 1 schematically illustrates an overall microfluidic system including a microfluidic device, controller, computer and sample material substrate.

The present invention generally provides novel devices for containing large numbers of potential pharmaceutical compounds in a stabilized addressable format for use in high throughput screening applications, as well as providing systems that integrate these devices with microfluidic elements, control elements and data acquisition and analysis elements, in high throughput screening applications.

Generally, the present invention provides a microfluidic device in which the fundamental aspects of the screening assay are carried out. Microfluidic devices for use in high throughput screening applications have been described in detail in U.S. Pat. No. 5,942,443, which is incorporated herein by reference for all purposes. Typically, such devices include a main analysis channel disposed within a substrate or body. The assay reactants are flowed along the analysis channels along with, at least periodically, a quantity or plug of a compound that is to be screened ("the test compound"). The effect of the test compound on the assay reactants is then ascertained. Although described as screening test compounds for effects against pharmaceutically relevant targets, it should be readily appreciated that the devices, methods and systems of the present invention are broadly applicable to a wide range of different high throughput analyses, e.g. diagnostic evaluations, nucleic acid analyses.

In order to bring large numbers of diverse test compounds into the channels of the microfluidic device, these devices are typically outfitted with a pipettor or sampling capillary element. Specifically, a pipettor element, i.e., a capillary tube, is typically provided extending from the body of the microfluidic device, and wherein the lumen or channel of the capillary element is in fluid communication with the analysis channel of the device, or another channel of the device that is in fluid communication with the analysis channel. The sampling element then samples the test compounds from the library storage component.

Library storage components have typically comprised multiwell plates filled with fluid reagents. The sampling element would simply be dipped into the wells of the multiwell plates and a sample of each test compound would be drawn into the sampling element. In accordance with aspects of the present invention however, the storage component comprises a collection of test compounds that are removably immobilized within separate discrete regions of a planar or substantially planar substrate, e.g., a sheet or card. The sampling element subjects these test compounds to appropriate conditions to remove the compounds from the surface of the substrate, e.g., by solubilizing dried compounds. The solubilized compounds are then individually drawn up into the sampling element and the microfluidic device, for analysis.

The overall systems of the present invention also typically comprise ancillary elements useful in carrying out the screening analyses, such as material transport systems and controls for directing material movement through the various fluid conduits of the system, robotic elements for controlling the relative positioning of the library storage element and the analysis system, e.g., the microfluidic device, detection systems, e.g., optical, electrochemical, thermal, etc., for detecting the results of the analysis that is being carried out within the microfluidic device, and a computer or processor for both controlling the operation of the system as a whole, and for recording and/or analyzing the data generated by the system.

FIG. 1 schematically illustrates an overall system in accordance with the present invention. As shown, the system 100 includes a microfluidic device 102 having a main analysis channel 104 disposed within its interior. A sampling pipettor or capillary 106 is attached to the device 102 such that the channel within the capillary (not shown) is in fluid communication with the analysis channel 104. A library storage substrate 108 is provided so as to be accessible by the capillary element 106. Typically, one or both of the device 102 and the library substrate 108 are provided mounted on an x-y-z translation stage 110 that moves one or both of these components relative to the other. Typically, the x-y-z translation stage 110 is automatically controlled, e.g., by a robotic positioning system (not shown). Such robotic x-y-z translation systems are generally commercially available from, e.g., Parker-Hannefin, Corp. In the case of preferred aspects of the invention, the x-y-z translation stage is optionally coupled to a sensor, illustrated as a box 150, that senses when the capillary element 106 is sufficiently proximal to the library storage substrate 108. The sensor 150 may be a stand-alone instrument or system, or may be incorporated into or made up of other components of the system, e.g., controller 120, computer 140 or detector 130.

The system also typically includes a controller instrument 120 operably coupled to the device 102 that controls and directs the movement of material through the channel or channels of the device 102. As described in greater detail below, the controller 120 may be an electrical controller, a pressure controller or the like. In the case of an electrical controller, operable coupling of the controller to the microfluidic device is typically accomplished via electrical leads and electrodes placed into contact with fluid reservoirs 112 in the device. In the case of a pressure based flow controller, the operable connection is typically provided by one or more vacuum or pressure lines coupled to the termini of one or more channels the device 102.

A detection system 130 is also typically provided within sensory communication of the one or more analysis channels 104 of the device 102. The detection system detects signals from the analysis channel and the data is collected, stored and/or analyzed by a computer or processor 140 that is operably coupled to the detector. As used herein, the phrase "within sensory communication" refers to a detector that is positioned within or sufficiently proximal to the analysis channel so as to receive a detectable signal from the contents of the channel. The computer 140 (or optionally, an additional computer, not shown) is also coupled to the controller 120 to control the movement of material within the channel (s) of the device 102 in accordance with a preprogrammed set of instructions.

While typically described herein as an overall system, it will be appreciated however that the present invention encompasses all of the components of the overall system, whether in the aggregate, or as separate and discrete elements. The various elements of the overall system are each described in greater detail, below.

II. Microfluidic Assay Devices

As noted above, the screening assay methods of the present invention are generally carried out within one or more microfluidic channels. As used herein, the term "microfluidic" refers to a fluidic component, e.g. a channel, chamber, reservoir, or the like, that includes at least one cross-sectional dimension, e.g., depth, width, length, diameter, of from about 0.1 $\mu$m to about 500 $\mu$m. Microfluidic devices having dimensions in these ranges are described in U.S. Pat. Nos. 5,942,443 and 5,880,071, each of which is incorporated herein by reference. Typically, such devices are planar in structure and are fabricated from an aggregation of planar substrate layers where the fluidic elements are defined in the interface of the various layers. Specifically, channels and chambers are typically etched, embossed, molded, ablated or otherwise fabricated into a surface of a first substrate layer as grooves and/or depressions. A second substrate layer is then overlaid and bonded to the first to cover the grooves creating sealed channels within the interior portion of the device.

In the case of planar microfluidic devices, substrate materials can be selected from a wide variety of different materials, provided such materials are compatible with the desired analysis to be carried out within the devices, and such substrates are compatible with microfabrication techniques. In preferred aspects, the substrate layers are individually selected from silica-based substrates (e.g., glass, quartz, silicon, fused silica, etc.), polymeric substrates (e.g., polymethylmethacrylate, polycarbonate, polytetrafluoroethylene, polyvinylchloride, polydimethylsiloxane, polysulfone, polystyrene, polymethylpentene, polypropylene, polyethylene, polyvinylidine fluoride, and acrylonitrile-butadiene-styrene copolymer, parylene), ceramic substrates, or the like.

Although described in terms of a layered planar body structure, it will be appreciated that microfluidic devices in accordance with the present invention may take a variety of forms, including aggregations of fluidic components, e.g., capillary tubes, individual chambers, etc., that are pieced together to provide the integrated fluidic elements of the complete device.

The microfluidic devices of the invention typically include at least one main analysis channel, but may include two or more main analysis channels in order to multiplex the number of analyses being carried out in the microfluidic device at any given time. Typically, a single device will include from about 1 to about 100 separate analysis channels. Preferably, each device will include more than 1, more preferably, 4 or more, still more preferably, 8 or more and often, 12 or more analysis channels.

In most cases, the analysis channel or channel is intersected by at least one other microscale channel disposed within the body of the device. Typically, the one or more additional channels are used to bring the test compounds and assay reagents into the main analysis channel, in order to carry out the desired assay.

Figure 2:
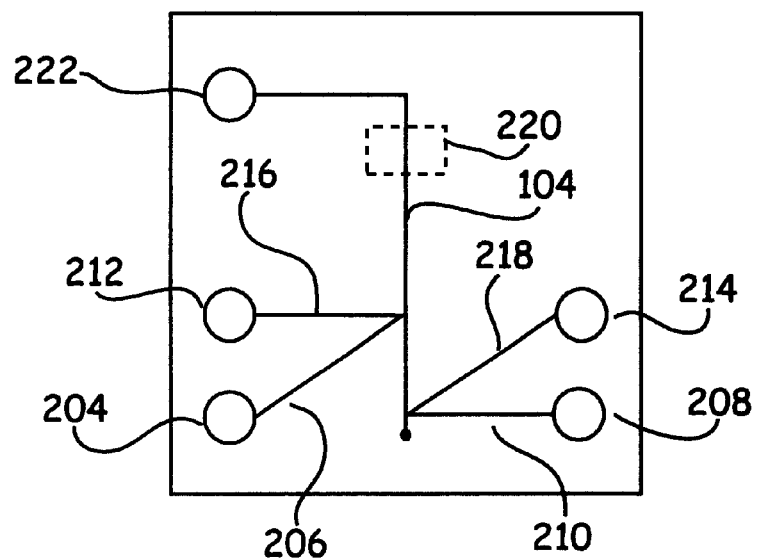
FIG. 2 schematically illustrates a microfluidic device for use in high throughput analytical operations.
Figure 2:
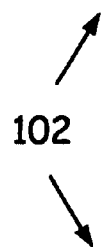
Figure 2:
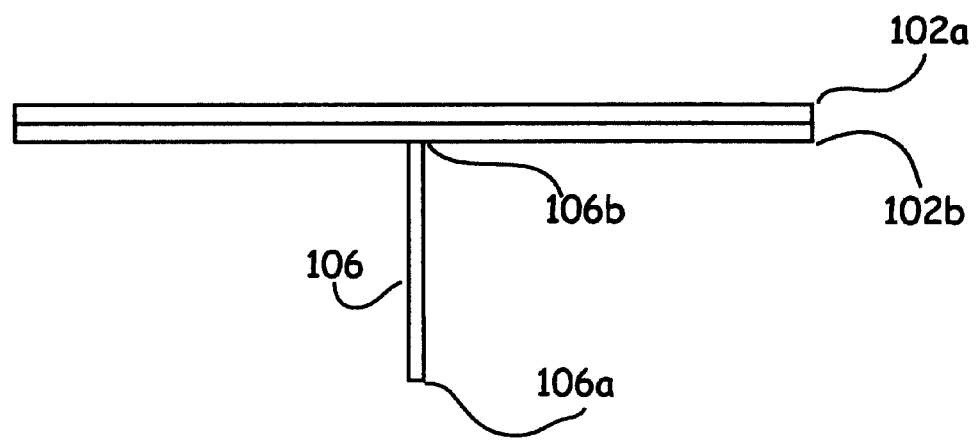
Figure 5A:
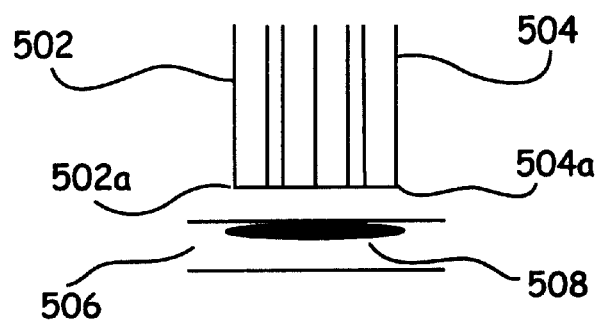
FIG. 5 illustrates a dual capillary embodiment of the sampling systems of the present invention.
Figure 5B:
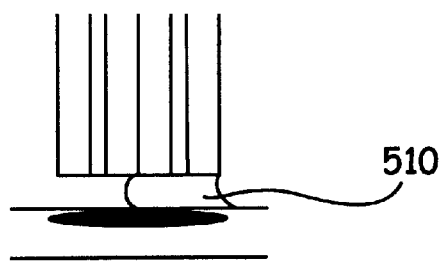
Figure 5C:
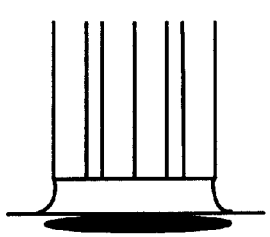
Figure 5D:
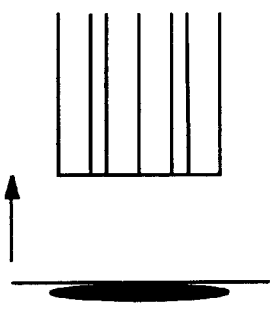

One example of a microfluidic device for carrying out high-throughput assays is shown from a top and end view in FIG. 2. As shown, the overall device 102 is planar in structure and is fabricated as an aggregation of substrate layers, e.g., layers 102a and 102b. The fluidic elements of the device, e.g., channels 104, 206 and 210, are defined in the space at the interface of the two substrate layers. Typically, this is carried out by etching, ablating, molding, or embossing one or more grooves into the surface of one or both of the two substrate layers which are typically either polymeric, e.g., plastic (see, e.g., U.S. Pat. No. 5,885,470), or silica based, e.g., glass, fused silica, quartz, silicon, or the like. When the second substrate layer is mated with and bonded or fused to the first substrate layer, these grooves are sealed to form conduits or channels within the interior of the body of the device.

Sampling capillary 106 is also provided attached to the device for accessing externally located sources of sample material, e.g., samples, test compounds, etc., that are being subjected to the assay in question. As shown, the sampling capillary 106 is open at one end 106a for accessing external materials, and is fluidly coupled to at least one channel in the body of the device 102 at the other end 106b.

In operation, assay reagents, i.e., enzyme and substrate, are typically concurrently flowed into the main analysis channel 104 from reservoirs 204 and 208 via channels 206 and 210, respectively. These reagents are optionally combined with other reagents, buffers or other diluents from reservoirs 212 and 214, respectively, brought into the main channel 104 via channels 216 and 218, respectively. Periodically, test compounds, sample materials or the like are introduced into the main analysis channel 104 from an external library via the external sampling capillary 106. For example, in one aspect, assay reagents are continuously flowed along the main analysis channel 104 producing a steady state signal at detection window 220 that is indicative of the functioning of the assayed system. When a test compound is introduced that has an effect on the assay system, e.g., as an inhibitor or enhancer of activity, it produces a deviation from the steady state signal.

The structure and/or operation of the sampling capillary or pipettor element 106 may vary depending upon the specific process that is to be used to sample materials from the library storage component. As described in greater detail below, the library storage component typically comprises substrate or substrate matrix that includes a large number of different compounds, samples or other materials to be assayed or screened that are reversibly immobilized upon its surface in discrete locations. As such, the pipettor element typically has the ability to present a volume of fluid at its open end, which fluid is used to solubilize or otherwise release the sample or test compound material from the library storage component.

In its first and simplest aspect, a single capillary or pipettor element is provided attached to the body structure of the device, e.g., as shown in FIGS. 1 and 2. As shown in FIG. 3, in operation, a spacer or solubilizing fluid is introduced into the capillary element by placing the open end 106a of the capillary element 106 into contact with a source, well or reservoir 302 of the spacer or solubilizing fluid, and drawing that fluid into the capillary channel 106c (Panel A). When the capillary is removed from the solubilizing fluid well 302 (Panel B), the surface tension on the fluid results in a small amount or drop 304 of fluid that remains suspended from the open end 106a of the capillary 106. This residual fluid or "hanging drop" is then moved over to an appropriate location on the library substrate 306 (Panel C). The hanging drop is then moved into contact with the surface of the library substrate 306 (and the compound or sample immobilized thereon), at which point the compound or sample on the library substrate dissolves or is otherwise released into the small volume of fluid that was the hanging drop. Once released from the substrate 306, the compound or sample material is drawn into the capillary channel 106c (Panel D) and then into the analysis channel of the device (e.g., channel 104 in FIG. 2) whereupon it is screened in the assay of interest.

FIG. 4 illustrates a variation of the simple method illustrated in FIG. 3. In particular, instead of relying upon a residual amount of resolubilizing fluid that adheres to the end of the capillary, the system is operated so as to expel a small volume of the resolubilizing fluid from the end of the capillary. This is useful in cases where larger amounts of fluid are desired for resolubilization than may be provided in a hanging drop. Typically, the fluid is expelled from the capillary end 106a when the capillary 106 is positioned over the appropriate location on the sample substrate 306 (Panel C, FIG. 4). Expulsion of a small amount of fluid is easily accomplished by simply reversing the flow direction in the capillary channel 106c. Typically, this is accomplished by either applying a slight positive pressure to the waste well of the device, e.g., well 222 in FIG. 2. Alternatively, in electrokinetically controlled aspects, the polarity of an electric field can be modulated to cause electroosmotic fluid flow in the desired direction, e.g., out of the open end of the capillary channel. Again, as with FIG. 3, the material released from the surface of the substrate is drawn into the capillary channel 106c and into the analysis channel for analysis.

Alternatively, a dual channel or dual capillary system can be used to provide the resolubilizing fluid onto the surface of the sample substrate. A second channel or capillary element is then used to draw the material from the surface of the substrate and into the analysis channel of the microfluidic device. An example of such a dual channel system is illustrated in FIG. 5.

As shown in panel A, the overall device (not shown) is similar to that shown in FIG. 2 except that an additional capillary element is provided fluidly coupled to a resolubilizing fluid reservoir. In particular, the device includes a main sampling capillary 502 and a fluid delivery capillary 504. Each of the fluid delivery capillary 504 and the sampling capillary 502 have an open end (504a and 502a, respectively) for expelling fluid onto the substrate surface 506 and drawing resolubilized sample materials 508 into the sampling capillary. Typically, the sampling and fluid delivery capillaries are disposed adjacent one another, e.g., as shown, so that fluid is delivered from the delivery capillary 504 and drawn up into the sampling capillary 502 without moving the overall device or library substrate 506. The fluid delivery capillary is fluidically coupled to a source of the resolubilizing fluid whereas the sampling capillary is fluidly connected to the analysis channel within the device (e.g., as shown for capillary element 106 in FIG. 2). The source of resolubilizing fluid may be integrated within the overall microfluidic device, e.g., as a well or reservoir in the overall body structure. Alternatively, the source of resolubilization may be partially or entirely separate from the microfluidic device. Although described as two discrete capillary elements, it will be appreciated that two capillary sized channels could be provided within one element that is attached to the body of the device where the sampling capillary channel is connected to the analysis channel, while the fluid delivery capillary channel is connected to a channel that leads to a resolubilizing fluid reservoir or well, e.g., as shown for reagent well 204 and channel 206 in FIG. 2. In particular, the sampling channel and the fluid delivery channel would be disposed within a single capillary or pipettor element that is attached to the body structure of the overall device, itself.

The operation of this system is also schematically illustrated in FIG. 5. In particular, the capillaries are positioned adjacent to an immobilized compound or sample 508 on the library substrate 506 (Panel A). Fluid 510 is expelled from the fluid delivery capillary 504 onto the substrate surface, whereupon the compound or sample material 508 is at least partially resolubilized into the expelled fluid (Panel B and C). A portion of the fluid on the substrate is then drawn into the sampling capillary 502 and into the analysis channel, as described above (Panel C). The capillaries 502 and 504 are then moved away from the substrate 506 (Panel D) to either draw in a spacer fluid plug to separate the resolubilized material from a subsequent sample material, or positioned adjacent another immobilized test compound for sampling.

As noted above, the particular spot or area of sample material, e.g., sample material 508, may be provided such that is substantially entirely solubilized and drawn into the sampling capillary 502. However, preferably, each sample material region includes sufficient material such that it can be sampled multiple times, e.g., 2, 3, 5, 10 or more times. This is discussed in greater detail herein, with respect to library substrates.

Although primarily described in terms of the preferred embodiments where the sampling pipettor or capillary is fluidly coupled to an analysis channel within a microfluidic device to which the capillary is attached, it will be appreciated that the methods and systems described above work equally well in non-integrated assay systems. For example, in one aspect, the solubilized sample material drawn into the sampling capillary is transported to a discrete and separate reaction vessel for analysis, e.g., by moving the pipettor or capillary over or within the reaction vessel or well, e.g., a well in a multiwell plate, or the like. The positioning of the vessel and/or the sampling capillary is typically accomplished by placing one or both of the vessel and/or the sampling capillary on a translation stage, e.g., a x-y-z translation stage, to move the vessel or capillary into the appropriate position relative to the other. Once positioned, the sampling capillary expels the solubilized sample material into the reaction vessel or well in which the desired analysis is carried out.

III. Sample Accession

As noted previously, the above-described microfluidic device carries out high-throughput experimentation by accessing a large number of diverse reagents from outside the device itself, e.g., from a reagent library. In the case of the present invention, this library typically takes the form of a card or substrate that has a large number of discrete quantities of different test compounds removably immobilized thereon. By "removably immobilized," is meant that the sample materials are present upon the sample substrate in an immobilized format, e.g., confined in a discrete region, but are removable from that substrate through appropriate action.

By way of example, samples that are deposited and dried upon the sample substrate are removably immobilized in that the dried reagents remain within their confined space, but are removable by dissolving them in fluid and pulling the fluid off of the sample substrate. A variety of other types of removable immobilization are optionally used in conjunction with the present invention. For example, structural barriers are used to confine liquid sample materials within a confined region of the sample substrate while permitting removal of those liquid sample materials. Similarly, porous sample matrices are optionally used to retain fluid reagents within a confined space on the sample substrate. Such sample materials are then removable by withdrawing the fluids from the pores of the substrate. Alternatively, sample materials may be coupled to substrate matrices, e.g., through ionic, hydrophobic or hydrophilic interactions, covalent but severable interactions, which couplings are severable by exposing the substrate to an appropriate environment, e.g., high or low salt buffer solution, organic buffer, thermal dissociation or release (e.g., where the matrix incorporates a thermally responsive hydrogel, which expands or contracts upon heating, to expel entrained compounds), light or other electromagnetic radiation (e.g., in the case of photolabile linker groups) etc. Such selectively releasable compound materials are also particularly useful in applications where particular compound locations are to be revisited multiple times, as discussed further herein. For example, a limited quantity of material can be released by the controlled exposure of the material to the cleaving agent or environmental conditions, e.g., heat, light, etc. Additional material is then released upon a subsequent visit using additional cleaving agents or environmental conditions. By way of example, if a particular compound deposit is tethered to the substrate using a photocleavable linker, a relatively precise amount of material could be released upon each visit by adjusting the intensity or duration of photoexposure of the compound deposit.

In particularly preferred aspects, the sample materials are provided dried upon or within the sample substrate. Typically, such sample substrates are readily prepared by any of a variety of different methods. In particular, simple pipetting methods are optionally used to spot the sample materials in discrete regions of the sample substrate. Alternatively, for higher density collections of sample materials, ink-jet printing methods are readily employed to print or direct fluid sample materials onto discrete regions of the sample substrate, whereupon they are lyophilized in place. These various methods optionally benefit from the presence of constraining regions on the surface of the sample substrate, e.g., raise barriers/depressions on the surface, hydrophobic barriers surrounding hydrophilic regions or vice versa.

In certain preferred aspects, the discrete quantities of sample material on the sample substrate are present in sufficient quantities or over a sufficiently large area so as to permit multiple samplings of each different sample material. In particularly preferred aspects, each discrete quantity of material on the sample substrate contains a sufficient amount of material to permit sampling from the material spot more than one time, preferably, more than two times, more than three times, often more than five times, and in some cases, more than ten times. Typically, the amount of material required for multiple samplings is dependent upon the nature of the sampling system used. Typically, each sampling will deposit an amount of solubilizing fluid that is 100 nl or less, preferably, 10 nl or less, and often, 1 nl or less. In accordance with the multiple sampling aspects of the system, the quantity of sample material should be only partially dissolved in the solubilizing fluid. By "partially dissolved," is meant that only a portion of the material in a discrete sample quantity is solubilized at a given time. The partial dissolution includes instances where the solubilizing fluid is only deposited upon a portion of the sample material region dissolving all of the material in that portion of the sample material region, or alternatively, deposited upon the entire sample material region but wherein the material is not completely dissolved.

Typically, screening assays are performed on compounds that are present at concentrations in the micromolar range, e.g., from about 1 to about 20 $\mu$M. In the present invention, compounds are typically sipped into the assay system in nanoliter range volumes. As such, if one assumes the dissolution volume, e.g., from a hanging drop is approximately 10 nl, then it is generally desirable to have the compounds present upon the surface in amounts at or in excess of about 5 femtomoles. Of course, depending upon the activity or efficacy of a given compound in a system, this amount can vary greatly. Similarly, these amounts can change significantly depending upon the number of times a particular sample spot is accessed. In general, each discrete quantity of sample material will contain between 0.5 pg and 100 ng of sample material, preferably, between about 5 pg and about 10 ng or between about 10 femtomole and about 20 picomoles of material and preferably between about 10 and about 1000 femtomoles of material. Typically, materials that are present in these amounts are more than adequate for 1×, 2×, and 3× and even upwards of 5× to 10× sampling from each spot. The spots are typically deposited in solutions that range from about 10 nM to about 10 $\mu$M. The concentration and amounts of compounds deposited upon the substrate surface typically depends upon the amount of material that is to be sampled, e.g., per sampling or in a number of samplings. Typically deposited compounds are present at quantities that are greater than or equal to about 1 pmole/mm$^2$.

In order to facilitate rapid solubilization of the sample material, in certain aspects, it is preferred to provide the sample material in a thin layer on the surface of the substrate (or its pores). For example, materials are typically deposited upon the substrate at concentrations and quantities calculated substantially to provide a molecular monolayer or near monolayer of the compound species. In some cases, materials are deposited at greater than monolayer quantities, often falling between about one and twenty times monolayer quantities.

For a porous substrate, e.g., a honeycomb matrix, because the sample material is entrained in the porous substrate matrix, the amount of surface area covered by a particular sample material is much greater per unit of external surface area than in the case of non-porous substrates. As such, much greater amounts of sample material can be provided in the same or smaller external surface area than in non-porous substrates.

The cards described herein are typically fabricated from any number of different materials, depending upon the nature of the material to be deposited thereon, the desired quantity of material to be deposited thereon, etc. For example, for some applications, the card comprises a solid non-porous substrate where the sample materials are spotted or deposited upon one planar surface of the card. Such substrates are typically suitable where it is less important to maximize the amount of material on the sample substrate. Examples of these non-porous substrates include, e.g., metal substrates, glass, quartz or silicon substrates, polymer substrates or polymer coated substrates including, e.g., polystyrene, polypropylene, polyethylene, polytetrafluoroethylene, polycarbonate, acrylics, i.e., polymethylmethacrylate, and the like.

Substrate surfaces may be of the base substrate material or may comprise a coating on a rigid substrate base. For example, in the case of glass substrates, the surface of the base glass substrate may be treated to provide surface properties that are compatible and/or beneficial to the reagents deposited thereon. Such treatments include derivatization of the glass surface, e.g., through silanization or the like, or through coating of the surface using, e.g., a thin layer of other material such as a polymeric or metallic material. Derivatization using silane chemistry is well known to those of skill in the art and can be readily employed to add amine, aldehyde, diol or other functional groups to the surface of the glass substrate, depending upon the desired surface properties. Alternatively, a glass substrate layer may be provided over the surface of another base substrate, e.g., silicon, metal, ceramic, or the like.

In the case of polymer substrates, as with the glass or other silica based substrates described above, the sample substrate may be entirely comprised of these polymer materials, or such materials may be provided as a coating over a support element, e.g., metal, silicon, ceramic, glass or other polymer or plastic card, e.g., to provide sufficient rigidity to the library substrate. In some cases, metal substrates are used either coated or uncoated, in order to take advantage of their conductivity, as described in greater detail below.

Further, in the case of metal substrates, metals that are not easily corroded under potentially high salt conditions, applied electric fields, and the like are preferred. For example, titanium substrates, platinum substrates and gold substrates are generally suitable for this reason, although other metals, e.g., aluminum, stainless steel, and the like, are also useful. Of course, for cost reasons, titanium metal substrates are generally preferred where no external coating is being applied.

Alternatively, where greater amounts of material are desired to be immobilized upon the card, porous materials are used. In particular, porous materials provide an increased surface area upon which sample materials may be immobilized, dried or otherwise disposed. Porous substrates include membranes, scintered materials, e.g., metal, glass, polymers, etc., spun polymer materials, or the like.

Examples of particularly useful porous substrate materials include substrate matrices such as aluminum oxide, etched polycarbonate substrates, etched silicon (optionally including a polymer or other compound compatible coating, and like substrates that comprise arrayed honeycomb pores, e.g., hexagonal pores. Such substrates are particularly preferred for their ability to maintain liquid samples within a confined area. Specifically, because of their porous nature, fluids deposited upon a surface of the matrix do not laterally diffuse across the substrate surface to any great extent. Instead, the fluids wick into the pores in the substrate. This property allows sample materials to be deposited upon the substrate matrix in relatively high densities without concern for samples diffusing together across the substrate surface or through the interstices of the matrix. In addition, the pores in the sample substrate provide a greatly increased surface area as compared to non-porous substrates, upon which greater quantities of sample material may be deposited in a monolayer or otherwise thin coating, as described in greater detail herein.

Other useful substrate materials include conventional porous membrane materials, i.e., nitrocellulose, polyvinylidine difluoride (PVDF), polysulfone, polyvinyl chloride, spun polypropylene, polytetrafluoroethylene (PTFE), and the like. However, honeycombed matrices are generally more preferred as far as porous matrices are concerned, due to their ability to contain the spotted materials within discrete sets of pores, rather than permitting their diffusion across or through the substrate.

As noted above, the type of sample substrate often depends upon the nature of the sample material that is to be deposited upon it. In turn, the sample materials to be deposited upon the sample substrate or card depend, of course, upon the type of screening application one is performing. For example, in pharmaceutical screening operations, the test compounds will range from complex organic substances to peptides, proteins, carbohydrates, nucleic acids and the like, which may have been produced in combinatorial synthetic processes or isolated from natural sources. It is then desirable to individually assay each material on the substrate in order to determine whether that compound possesses any useful pharmacological activity.

For other screening applications, sample materials in accordance with the present invention include biological macromolecules, e.g., proteins, peptides, nucleic acids or fragments thereof, including, DNA, RNA, double or single stranded, peptide nucleic acids (PNA), lipids, etc. In the case of these latter compounds, the sample substrate also can serve as an array of sources of material for analysis of a particular sample material. Specifically, sample substrates may be provided with arrays or collections of different oligonucleotide probes, primers, or the like. Such collections or arrays are then selectively accessible by a microfluidic device or system whereby the probes or primers can be used to examine a sample material, e.g., a target nucleic acid, for identification, sequencing or the like (see, e.g., Published International Patent Application No. WO 98/45481, which is incorporated herein by reference in its entirety for all purposes. Such collections of materials are useful in a variety of research and diagnostic fields, including nucleic acid sequencing, characterization, diagnostics and the like.

The sample substrates of the present invention typically include relatively large numbers of different sample materials within relatively small substrate areas. In particular, the sample substrates described herein typically include at least 10 different and discrete quantities of sample material immobilized, dried or otherwise contained within a square cm of substrate surface area. In preferred aspects, the sample materials are present at a density greater than 100 samples/cm2, preferably, greater than 500 samples/$cm^2$, often greater than 1000 samples/$cm^2$, and in some cases, more than 10,000 samples/$cm^2$. As noted above, preparation of high-density arrays of sample materials is facilitated by the use of ink-jet or related fluid direction systems (see, e.g., U.S. Pat. No. 5,474,796, as well as by the use of appropriate low diffusion sample substrate materials. Alternatively, pin or quill based contact printing or spotting methods may be readily employed, where a pin or quill is first dipped into the reagent of interest. The pin, with a quantity of material on its end, is then contacted with the surface of the reagent array substrate, whereupon the material is transferred to that surface. Arrays of pins/quills are used simultaneously to sample from multiple reagent sources, e.g., wells in a 96, 384 or 1536 well plate and transfer material to the surface of the reagent array substrate.

In certain preferred aspects, the samples that are reversibly immobilized on the surface of the sample substrate are provided in a form that permits easier deposition, drying, release and/or solubilization of those compounds from that surface, depending upon the particular application that is contemplated. For example, in one optional embodiment, compounds that are spotted and dried onto the substrate surface comprise, in addition to the particular compound or compound mixture, include at least one excipient material that enhances one or more of the deposition and/or the solubilization of the compound in the appropriate solubilization liquid. Such excipients also function as binding agents for the dried compound to enhance the deposition of the compound material on the substrate. Similarly, excipient materials can aid in the controlled dispersion of liquid on the surface of the substrates during the spotting operation. Examples of excipients include starches, dextrans, glycols, e.g., PEG, other polymers, e.g., polyethylene oxide, polyvinylpyrrolidone, detergents as well as simple sugars, e.g., sucrose, fructose, maltose, trehelose, and modified versions of these, and the like. The excipient material is typically provided as a mixture with the various test compounds or compound mixtures, which are then spotted onto the substrate surface and dried.

Alternatively, or additionally, the test compounds are dried on the substrate surface by a freeze drying that yields test compounds that are generally in a more soluble format, e.g., by virtue of their greater surface area. In particular, freeze drying techniques typically result in materials that are "fluffier" in terms of their physical state, and are therefore more easily dissolved. A variety of other drying methods may be employed depending upon the nature of the reagents being provided on the array substrate, including heat drying, vacuum drying, drying under controlled atmosphere, e.g., alkane or alcohol vapor, or the like.

In addition to providing a source of different test compounds, reagents or the like, in some aspects, the sample substrate optionally functions as an intermediate staging area for the operations that are performed within the channels of a microfluidic device or as a holding area for slower reactions, and the like. Specifically, a portion of, or an entire sample substrate can be used to, e.g., premix several reagents, stage randomly accessed reagents, and/or provide multiple dilutions of particular reagents, prior to introduction into the microfluidic device.

In some cases, reagents that are to be combined in a particular reaction are less compatible with the mixing kinetics of a microfluidic device, e.g., they diffuse or react so slowly that there is insufficient time to mix and react reagents during the rapid processing operations of a microfluidic system. For example, molecules having slow diffusion kinetics include large molecules or molecules in viscous medium. Reagents that have slower reaction kinetics, e.g., certain enzymes and substrates, are also optionally mixed outside of the channels of a microfluidic device, and allowed to react for a set time before being sampled into the channels of the microfluidic device. Alternatively, one may wish to mix several different reagents for a particular analysis, which in a capillary channel can require substantial diffusion times, e.g., for serial plugs of material to completely diffuse into each other. As such, in accordance with certain aspects of the invention, one can deposit various reagents that are to be mixed upon a portion of a sample substrate where the reagents are permitted to mix for sufficient time. The resulting mixture is then sampled into a microfluidic device as described herein. Typically, such mixtures can include a first reagent combined with a second reagent, and alternatively a third reagent, fourth reagent and fifth reagent can be added, either to the first and second reagent as a complete mixture, or as separate combinations in different portions of the intermediate sample substrate.

Relatedly, one can mix different combinations of reagents onto a portion of a sample substrate prior to introducing the mixtures into a microfluidic device. For example, one could deposit a first reagent in multiple regions of a sample substrate, and add to that reagent multiple different reagents, which would then be introduced into a microfluidic device. This allows one to perform a pseudo-combinatorial process of reagent combination and addition. Additionally, such staging allows for mixing different reagents for introduction into a multiple sipper capillary system, e.g., where fixed capillary elements cannot randomly access all reagents in a sample array. In particular where a microfluidic device employs multiple accession capillaries having regular rigid spacing, one cannot randomly access different samples with each of the different capillaries, e.g., each sampling accesses multiple samples that are on the same spacing as the capillaries, which spacing does not change. Accordingly, in order to access a different combination of samples in a multiple capillary system, it is useful to reposition one or more samples on an intermediate staging substrate in an orientation that is different from the orientation that such samples had in the original sample substrate. The repositioned samples, test compounds, reagents, etc., then may be simultaneously sampled by a multiple capillary device where such simultaneous sampling could not have occurred in the original orientation of the samples in the original sample substrate array.

In a further related aspect, one can separately hydrate compounds before sipping them into the capillary element as adjacent plugs, e.g., to allow mixing and reaction within the capillary element or any associated channel. Extrapolating this, one can also hydrate and sip a first reagent into a capillary element, and then use that hydrated reagent to hydrate a subsequent reagent, e.g., through aspiration of the hydrated first reagent from the capillary or as a hanging droplet of the first reagent.

Finally, in addition to mixing reagents with other reagents, one can use the intermediate staging process to mix reagents with diluent in order to provide one or multiple different dilutions of the particular reagent or reagents prior to introducing it into the microfluidic device.

The portion of the sample substrate that is to be used as the staging area can be on a discrete sample substrate, or it can be a previously unused region of the sample substrate from which test compounds are originally obtained. In order to utilize the staging aspect of the sample substrate, one can deposit the reagents into particular regions of the sample substrate using a variety of methods. For example, well-known pipetting methods may be utilized to add reagents to the surface of the sample substrate. Alternatively, printing techniques, e.g., ink-jet printing techniques can be used for this reagent staging in much the same way such methods are utilized in spotting test compounds onto sample substrates, as described herein. In certain preferred aspects, a pipetting system similar to the accession systems employed in conjunction with the microfluidic devices described herein is employed. Specifically, a microscale capillary element is used in conjunction with a pumping system, e.g., a vacuum pump to draw different reagents into the capillary and then dispense those fluids onto the intermediate staging substrate. The different reagents are optionally sampled iteratively into the capillary and then dispensed en masse, onto the substrate, or they are individually sampled and dispensed successively onto the substrate.

The present invention also provides the above-described sample substrates in conjunction with a high-speed, highly accurate sampling system for sampling the sample materials from the sample substrate, and transporting those materials to an analytical element where the sample materials are scrutinized, e.g., for content, make-up, or effect on other systems, e.g., biological systems. In particular, the sampling system typically comprises a pipetting or capillary element, e.g., as described in substantial detail, above.

As alluded to above, because the sampling systems of the present invention contain large numbers of discrete sample materials for assaying in very small areas, the system for accessing these materials must be highly accurate and very fast. For example, in contacting a droplet on the end of a capillary element with a substrate, it is often necessary to position the capillary to within a matter of microns, e.g., 10 to 500 μm from the substrate surface, to allow the droplet to contact that surface. However, surface variations in substrates typically makes it difficult to program such positioning ahead of time, so as to yield consistent positioning of the capillary element relative to the substrate.

Accordingly, the systems of the present invention include a sensor component for detecting when the droplet on the capillary end has contacted or is positioned sufficiently proximal to the surface of the substrate. Generally, a capillary element or the drop disposed thereon is sufficiently proximal to the substrate if is within 1 mm or less, typically, 0.5 mm, 0.2 mm, 0.1 mm or even less, and typically is actually contacted with the substrate. In preferred aspects, optical or electrical sensor systems are utilized in performing this function, e.g., to sense whether the droplet has been contacted with or moved sufficiently proximal to the substrate surface.

Figure 6:
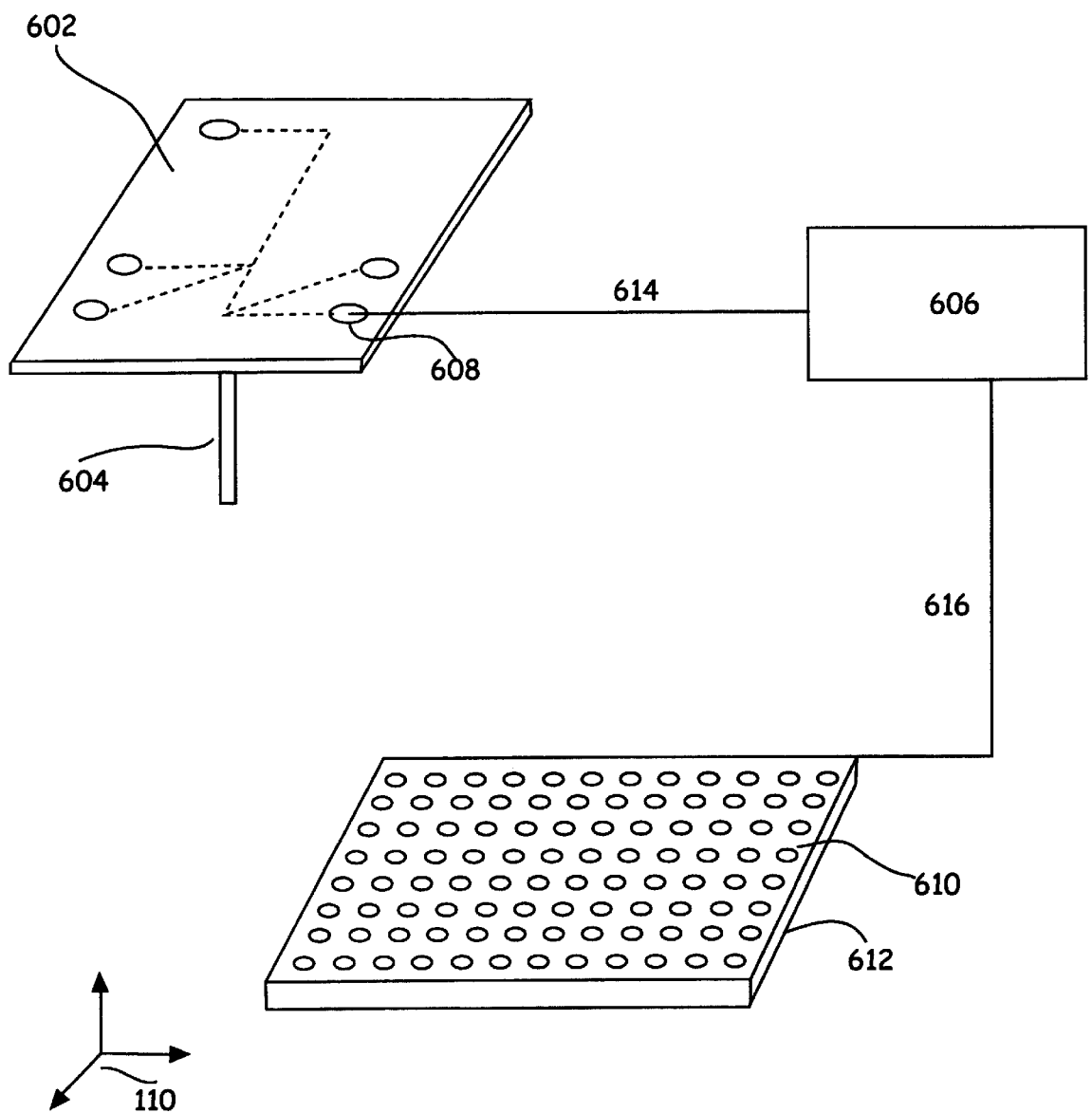
FIG. 6 schematically illustrates an electrical sensing system for sensing contact between the fluid at the end of the capillary and the sample substrate.

For example, in at least one aspect, an electrical signal is used to sense when the drop contacts the surface of the card. FIG. 6 is a schematic illustration of an example of a sensing system according to the present invention. As shown, the system 600 includes a microfluidic device 602 that comprises a capillary element 604. A lock-in amplifier 606 is also provided which is connected to the fluid within the microfluidic device and capillary element, e.g., via an electrical lead 614 to a reservoir or well 608. Optionally, the lock-in amplifier is substituted with a capacitance or conductivity meter. The lock-in amplifier is also connected to the sample substrate 610, or the support element 612 underlying the sample substrate, e.g., via lead 616.

In general operation, a current is applied to the circuit shown in FIG. 6, e.g., through leads 614 and 616. In this system, the "droplet-air gap-sample substrate" functions as a capacitor. The phase of the current relative to the current in a reference channel is a function of the relative impedances of the capacitor and any resistive impedances (such as the resistance represented by the fluid in a channel or capillary) in the circuit. As used herein, a reference channel typically includes a simple electrical circuit that is independent of the circuit through which capacitance is being measured, and lacks the varying capacitance of the fluid channel-droplet-air gap-substrate capacitor. In the case of the particular circuit shown, the lock-in amplifier 606 applies an alternating voltage to lead 616, the capacitance and/or resistance between the substrate and the droplet on the capillary 604 and fluid results in a current in lead 614, which is measured by the lock-in amplifier via a low impedance input. The magnitude and phase of the current in lead 614, compared to the voltage in lead 616 indicates the capacitive and/or resistive coupling from the substrate through the capillary. Optionally, the voltage can be applied on lead 614 and current can be measured on lead 616 or the current can be measured on the voltage applying lead.

Besides simply looking at the phase of the current travelling through the circuit, one can also monitor the component of the current that is 90 degrees ahead in phase of the reference current or applied voltage, since this corresponds to the capacitive portion of the circuit. The presence of capacitance in the circuit results in a shift in the phase of an alternating current coupled through the circuit, e.g., relative to a reference signal/applied voltage. Thus, where the droplet is separated from the substrate surface, e.g., by moving the substrate relative to the droplet on x-y-z translation stage 110, the capacitance of the "droplet-air gap-sample substrate" portion of the circuit is changing. The change in capacitance becomes increasingly fast as the drop approaches the surface of the sample substrate, thus yielding an increasingly fast change in the phase of the current. Contact between the drop and the substrate, which is also accompanied by a change in the geometry of the drop, yields further changes in the phase of the current. The sum of these changes is a rapid and detectable change in the phase (or equivalently, the component of the current 90 degrees ahead in phase of the reference signal/applied voltage) that occurs when the drop contacts the surface of the substrate. By monitoring the phase shift of the current through the circuit as noted above, one can monitor the relative proximity and even contact of the droplet with the surface. In FIG. 6, the system is illustrated as having the electrical connection to a reservoir of the overall microfluidic device such that the sensing current is applied through the channels of the device and the capillary element. However, it will be readily appreciated that this is primarily for convenience. Specifically, in certain aspects, it may be desirable to provide the electrical connection for applying this current into the droplet of fluid at the end of the capillary, e.g., through an electrode arrangement. Typically, this is accomplished by providing an electrically conductive layer along the outer surface of the capillary element such that a fluid droplet at the end of the capillary element will be in contact with the conductive layer. This layer may be a coating over the outer surface of the capillary element or may be patterned or otherwise deposited on that outer surface or a portion thereof.

Although described in terms of measuring the phase of the current applied through the capacitive portion of the circuit, it will be appreciated that the presently described sensing methods rely either directly or indirectly on a measurement of the changes in the capacitance of the overall circuit as a measure of the proximity of the drop to the surface. Capacitance measurements may take the form of phase measurements as described herein, or may be direct measurements of the capacitance of the circuit, e.g., using a capacitance meter. As described in greater detail herein, other electrical parameters also provide a basis for measurement.

Because the system relies upon the capacitance of the circuit, it enables the surface of the substrate to be a thin, non-conductive layer overlaid upon a conductive supporting member, e.g., from about 10 $\mu$m to about 1000 $\mu$m, and preferably from about 10 to about 500 $\mu$m thick. In particular, it is often desirable to retain the sample materials on inert substrates so as to avoid any adverse interactions between the sample material and the substrate surface. Typically preferred inert layers include, e.g., polytetrafluoroethylene (Teflon™), acrylic, e.g., PMMA, polypropylene, polystyrene, polycarbonate, metal oxides, $SiO_2$, $Si_3N_4$, silicon oxynitride and the like. In alternate aspects, however, conductivity is optionally used as the electrical signal. In particular, completion or closing of the overall circuit by contacting the drop of fluid with the substrate surface is detected and used as the indicative signal. In such cases, it is generally preferred to utilize a substrate surface that is conductive, e.g., a metallic substrate such as aluminum, titanium, platinum, gold, stainless steel, or the like, or semiconductive, e.g., silicon. In these cases, a current applied to the circuit can be alternating or direct. In addition, the system, while clearly capable of sensing actual contact between the droplet and the substrate surface also is capable if sensing when the droplet approaches the surface, allowing one to sense an electrical signal that is indicative of the distance between the fluid and the substrate, rather than sensing actual contact.

In addition to electrical sensing systems, optical sensing systems may also be used in this aspect of the invention, e.g., optically sensing when the drop has contacted the surface of the substrate. As used herein, the term "optical sensing" specifically excludes the direct observation of the contact between the drop and the substrate by the human eye. Instead, an automatic and/or remote sensing operation is envisioned. In at least one aspect, light from a light source is directed down the capillary element. As the light exits the capillary, it diverges. The light exiting the capillary reflects from, or in some cases excites fluorescence on the surface of the substrate.

In preferred aspects, the substrate surface is itself fluorescent or has a fluorescent material associated with it, e.g., coated thereon. The fluorescent material may be coated directly on the surface or it may be incorporated within another surface coating, e.g., a polymeric material. In some aspects, e.g., where a very thin translucent polymeric layer is applied as the surface of the substrate, the fluorescent coating may be applied underneath the polymeric layer, so as to not interfere or intermingle with any of the chemical compounds or other materials on the surface of the substrate.

While the capillary is distant from the substrate surface, the reflected or fluoresced light collected back through the capillary is significantly reduced by divergence of the light upon leaving the capillary, which results in a lower power density of incident light on the surface of the substrate. Divergence of the reflected or fluoresced light from the surface of the substrate also results in lower levels of recollected reflected or emitted light from the surface. However, as the capillary element is moved closer to the substrate, the light exiting the capillary is not permitted to diverge as far before being incident on the substrate surface. Further, the capillary collects a larger percentage of the reflected or fluoresced light, which is then detected. By setting a minimum threshold of collected light, or sensing a dramatic change in the collected light, one can then determine that the capillary is sufficiently close to the substrate surface. Changes in the geometry or shape of a drop at the end of the capillary also can have an effect on the level of collected light.

Figure 7A:
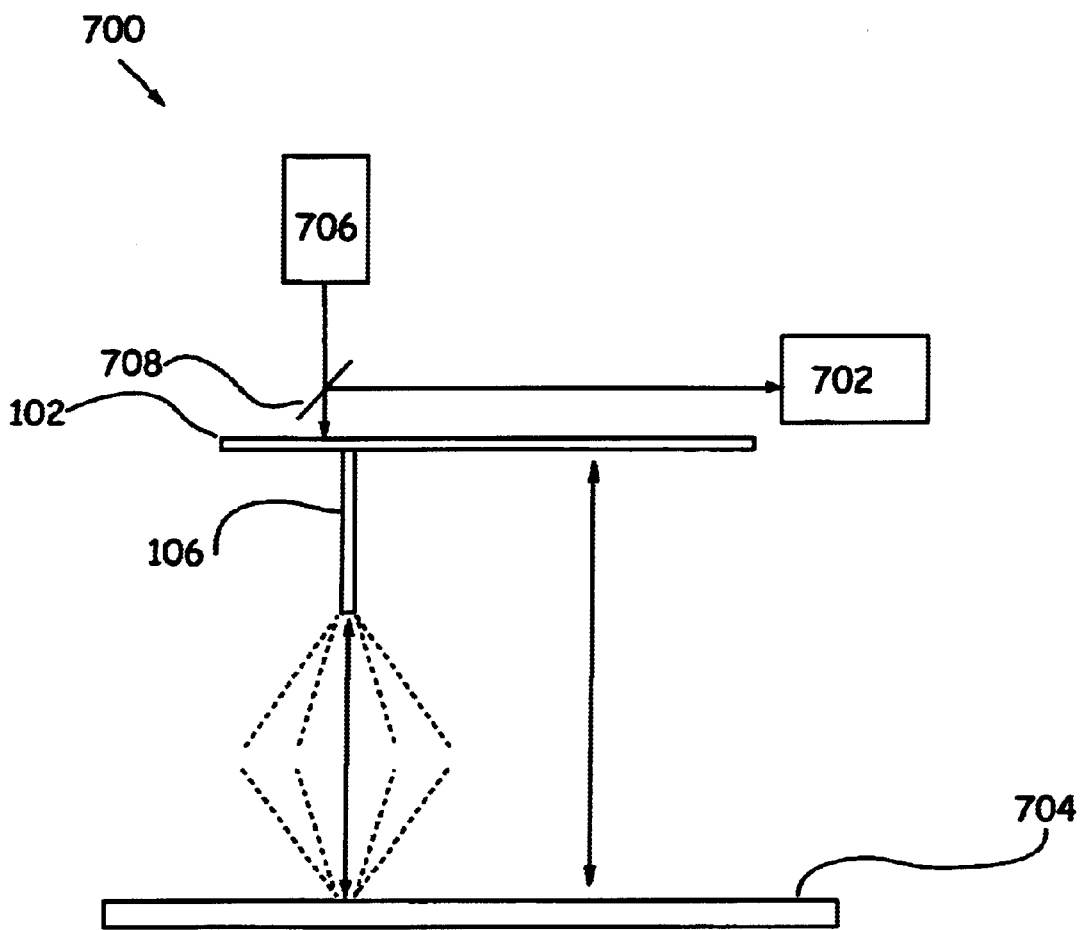
FIGS. 7A, 7B and 7C schematically illustrate alternate optical sensing systems for sensing contact between the fluid in the capillary and the surface of the sample substrate.

A schematic illustration of an exemplary optical detection system is illustrated in FIG. 7A. As shown, the system 700 includes a microfluidic device 102, e.g., as shown in FIG. 1, which includes a capillary element 106. Light from a light source 702 is directed down through the capillary element 106 which functions as a light pipe. Upon exiting the open end of the capillary 106a, the light diverges and is incident upon the surface of substrate 704, upon which reagent and/or sample materials are spotted or otherwise deposited. Reflected light and/or emitted fluorescence from the surface of the substrate also diverges, with a fraction of the reflected or emitted light being collected back through the capillary element 106. This fraction of collected light is then passed up through the capillary element 106, through the top layer of the microfluidic device 102, and directed to a detector 706, through an optical train, as represented by beamsplitter 708 (however, more complex optical trains are also envisioned, including objective lenses, spatial and spectral filters, additional dichroic beamsplitters and the like). When the substrate is moved closer to the open end of the capillary element 106, the light is not permitted to diverge as far before being incident upon the surface of substrate 704. This results in a higher power density for the light incident upon the substrate surface, which in turn yields greater reflected or fluoresced light. Further, because the capillary 106 is closer to the surface of substrate 704, the reflected or emitted light is not permitted to diverge as far before being collected by the capillary 106, resulting in a higher percentage of collected light. This higher percentage is then detected and compared to a threshold level to determine whether the capillary is sufficiently close to the substrate surface.

Relatedly, once the substrate is contacted, the amount of fluorescence emitted from the surface and collected through the capillary will not change, despite movement of the substrate relative to the surface. Thus, monitoring a stabilization of fluorescence levels also provides an indication of contact between the capillary end and the substrate surface. Of course, this method is less preferred as it requires contact between the capillary end and the substrate surface, which can potentially have adverse effects on the capillary, the substrate surface and/or materials deposited on the surface.

Although generally described in terms of methods of measuring light transmission of the capillary/drop/substrate system as a method of monitoring the relative positions of the capillary and the substrate, optical methods also include imaging systems. Specifically, in certain aspects, an optical sensing system comprises an imaging detector, e.g., a camera, CCD, or the like, disposed adjacent to and focused upon the capillary element and substrate surface. The imaging detector is operably coupled to a computer. The computer, programmed with image analysis software, recognizes from the image detector when the capillary element is sufficiently proximal to or contacting the substrate surface. One example of an imaging based system for monitoring sampling from a library card is illustrated in FIGS. 7B and 7C, from a perspective and side view, respectively.

Figure 7B:
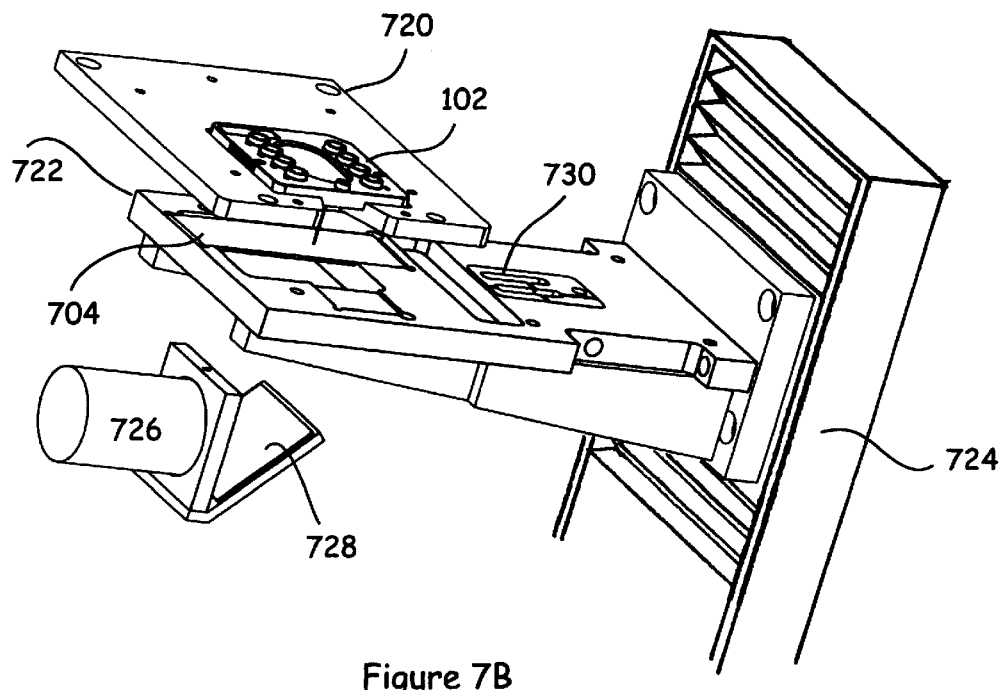
Figure 7C:
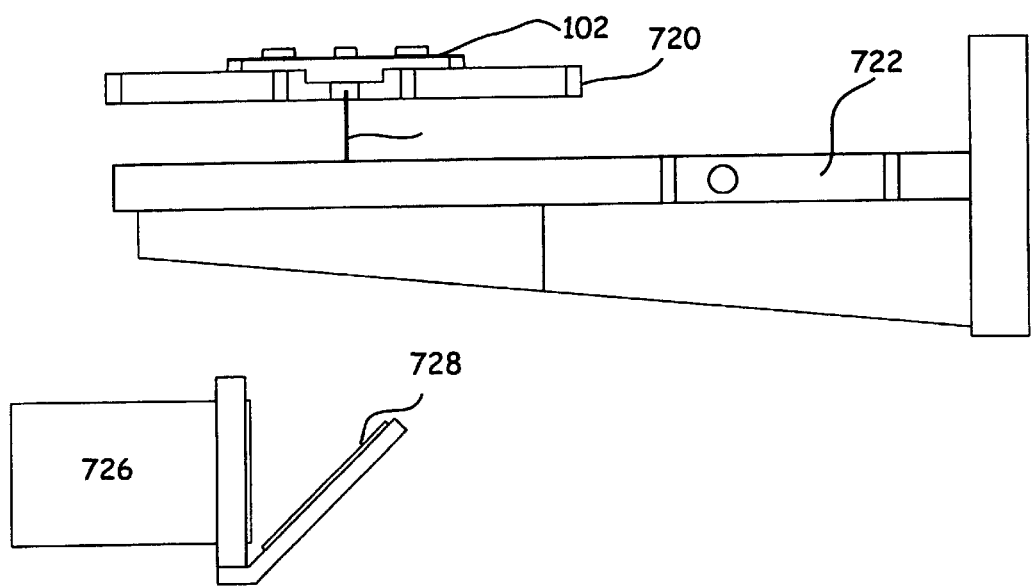

As illustrated in FIGS. 7B and 7C, the overall system includes a reagent library card or array substrate 704 as described above upon which is deposited a number of discrete quantities of material or materials (not shown). As described above, such materials may be dried or otherwise reversibly immobilized on the surface of the reagent array. In the particular embodiment illustrated in FIGS. 7B and 7C, the reagent array substrate 704 is fabricated from a transparent material, e.g., glass, quartz, or a transparent or translucent polymeric material, e.g., polycarbonate, acrylic (e.g., PMMA), polystyrene, or the like. A microfluidic device 102 that includes one or more external sampling capillary elements 106 is positioned above the array's surface such that the sampling element(s) are capable of being moved down to sample the materials from the surface of the array substrate 704. As shown, the microfluidic device 102 is placed onto a platform 720 that supports the device 102 over the array substrate 704, while the array substrate is placed on platform 722 that supports the array substrate 704 beneath the microfluidic device 102. One or both of platforms 720 and 722 are mounted on an x-y-z translation robot (partially shown as robot arm 724) to move the array and the microfluidic device relative to each other. As shown, platform 722 also includes an optional reagent trough 730 for sampling reagents, buffers or the like that are used consistently throughout a number of separate analyses.

A video imaging system, e.g., a camera 726, CCD, or the like, is positioned below the array substrate and images the array substrate 704 from the underside. As shown, the camera images the underside of the array substrate 704 via an angled mirror 728 that reflects the underside of the array toward the camera 726. When the sampling element is robotically moved down to the surface of the array, such that a droplet of fluid at the end of the sampling element contacts the material on the array surface, the imaging system records the event through the transparent array substrate 704. In alternate aspects, one or more additional imaging systems or cameras may be provided, e.g., directed at the sampling element and sample array substrate from the side, to permit more accurate imaging of the distances, and thus, the contacting event, between the sampling element and the substrate surface. It will be understood that either the array or the microfluidic device or both may be moved to contact the sampling element with the surface of the array. In preferred aspects, it is the reagent array substrate that is primarily moved toward the sampling element of the microfluidic device, so as to avoid moving the detection and control elements associated with the microfluidic device. Image analysis software then recognizes that the sampling element has contacted the surface of the array. This is preferably accomplished by the system recognizing the contact of fluid at the end of the capillary element with the surface of the array. However, in those cases where the camera or imaging system is focused on the end of the sampling element, e.g., for position alignment as described below, contact or near contact with the surface of the array may be indicated when the spotted materials on the surface of the array come into focus in the imaging system, e.g., the sampling element has moved sufficiently close to the surface such that both the end of the sampling element and the surface of the array are in the focal plane of the imaging system. Again, image analysis software is readily configured to recognize these events.

Recognition of contact or near contact with the array surface then stops the advancement of the robot. The sample material is then drawn into the sampling element for analysis within the microfluidic device, and the robot then lifts the sample away from the card surface and moves the sampling element to sample additional materials, e.g., spacer buffers and/or additional immobilized samples.

The imaging system is also used in conjunction with alignment of the sampling elements to the reagent regions on the surface of the array substrate. In accordance with preferred aspects of the present invention, the reagent materials that are immobilized on the array are positioned in a regularly spaced rectangular grid, e.g., spotted in one or more rows of compounds in a gridded format at regular intervals. The spacing of the materials typically depends upon the number of different material that are to be spotted onto the array, the available surface area of the array, the desired quantity of material in each spot, etc. As such, specific dimensions for spacing can vary greatly. Typically, materials will be positioned to be within one to several millimeters of adjacent spots, and will be oriented in rows and/or columns of spots. Because of their regular gridded spacing, the system is aligned by locating outer spots in the grid and interpolating those that fall between. For example, in multiple row grids, location of the various compound locations on the substrate involves location of the four corner most spots on the array, e.g., through manual alignment or through the inclusion of markers in the spots or on the substrate that permit their automatic location, and calculating or interpolating the position of all of the spots that are located between those four corners. In general, alignment can rely upon location of two points on a particular row, or on location of any three spots on an array of multiple rows to identify where the remaining spots are located, although using the four corner spots permits the highest confidence in the alignment procedure. In some cases, where one has identified the relative position of the first spot accessed, one can extrapolate the location of all other spots in the array. For example, if one first locates one or more given spots, knowing the relative location of those spots, the orientation of the array, etc., one can then interpolate and extrapolate the location of the other spots on an array. In such cases, it is not necessary that the first identified spots be located at the ends of any given row or rows in the array, e.g., the four corners.

In operation, the system moves the sampling element to a position that is close to the expected position of one of the corner spots (the "first position"). The sampling element is then aligned to the first spot by locating that spot with the imaging system and analysis software, and adjusting the positioning of the array using the x-y translation of the robotics system. The first spot may be located by virtue of its own optical properties, e.g., fluorescence, opacity, etc., or it may be located by virtue of a fabricated alignment mark on the array, e.g., a mark in the array or on its upper or lower surface that corresponds to the location of the first spot. The location of the first spot is then recorded and the process is repeated with the second and third corners. As noted, this provides sufficient information to locate all of the spots in the array. In order to verify that the positions have been properly identified, the fourth corner is then located (by virtue of the calculations made from the first three corner positions. This allows a positive confirmation of positioning process.

As noted previously, contact between the end of the sampling element or capillary and the surface of the array substrate can result in a number of problems, including inconsistencies in sampling materials from the array surface. Further, in the case of multiplexed systems, multiple capillary elements may be required to simultaneously access multiple reagent spots on an array. Due to variations in manufacturing of both the array surface and the length of the sampling elements, it would generally be very difficult to ensure the appropriate tolerances required to guarantee access to multiple reagent spots simultaneously, e.g., some capillaries may contact the surface of the reagent array while others remain a small distance from the surface. As noted, this can result in differing abilities of the capillary to pick up solubilized reagents from the surface of the reagent array substrate.

Figure 17A:
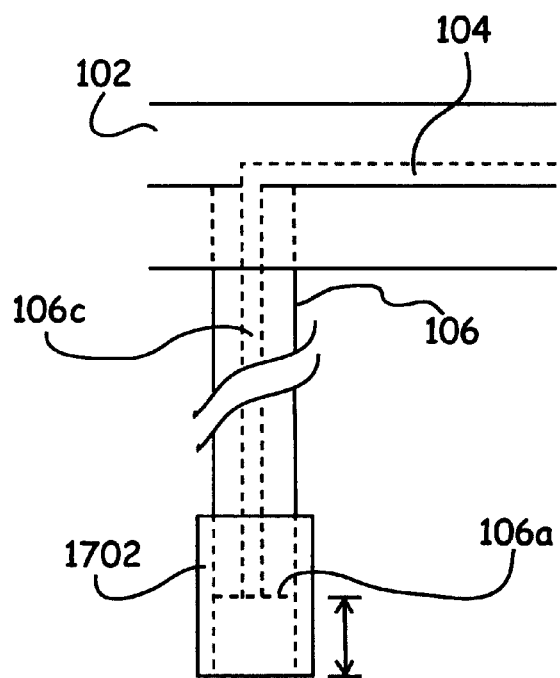
FIG. 17 schematically illustrates a sleeve offset structure for providing a fixed offset of sampling elements from reagent array substrates.

In order to optimize consistency in sampling, both in a single capillary from spot to spot, as well as from capillary to capillary, e.g., in multiple capillary systems, certain embodiments of the microfluidic devices of the present invention are provided with a fixed offset sleeve or frame (both are referred to herein as a sleeve), that prevents the capillary end from directly contacting the surface of the array, and maintains the end at a fixed distance from the surface of the array during the sampling operation, either by virtue of en enclosed cylinder of the extended sleeve, or through a tripod or dipod-like structure at the open end of the sleeve. In the case where a sampling element contacts the surface, the sleeve or frame maintains the open end of the sampling element a set fixed distance from the surface. In the case of multiple sampling elements, the sleeve maintains the open end of each element a set fixed distance from the surface. Even if one element is longer than another, the system moves the substrate and/or microfluidic device, relative to the other until all of the sleeves on the sampling elements have contacted the surface of the reagent array substrate. Where one element is longer than the other, that element merely deflects in response to the pressure of contact with the surface until the other sampling elements are brought into contact with the reagent array substrate surface. This portion of the present invention is illustrated in FIGS. 17A, B, C and D. Elements that are common to FIGS. 1 and 2 and FIG. 17 are referenced with common reference numerals.

Figure 17B:
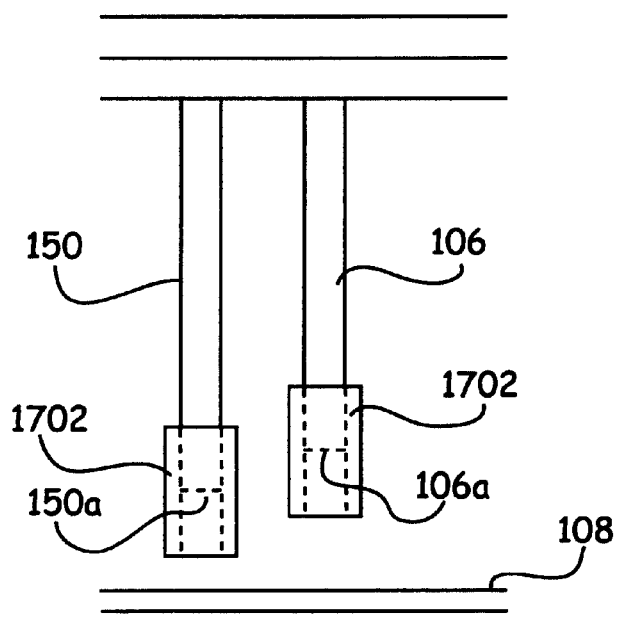
Figure 17C:
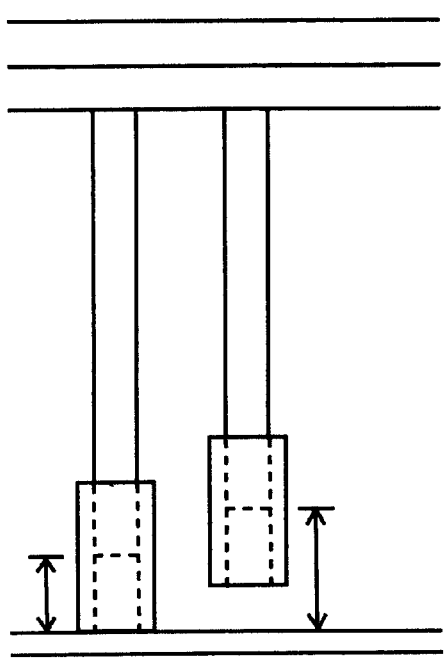
Figure 17D:
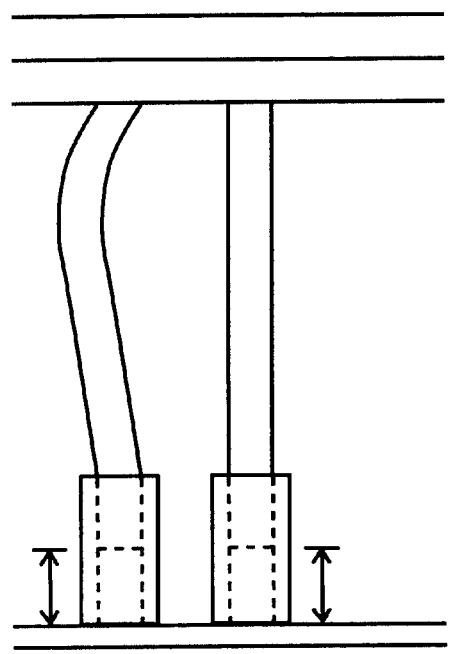

As shown in FIG. 17A, a microfluidic device 102 includes an external sampling element or capillary 106 that includes a channel 106c that is in fluid communication with a channel 104 in device 102. A sleeve 1702 is provided fitted onto the open end 106a of sampling capillary 106, such that the sleeve extends a set distance (as shown by the arrows) beyond the end 106a of capillary 106. FIGS. 17b, C and D illustrate a device 102 that includes multiple capillary elements, e.g., sampling elements 106 and 150, where the lengths of the various sampling elements have differing lengths, making simultaneous sampling with each element difficult. Each of the multiple sampling elements is provided with a sleeve 1702 that provides the same degree of offset for each sampling element, e.g., each sleeve extends a set distance beyond the end of each sampling element. In FIG. 17C, the longer sampling element 150 is shown contacting the surface of the reagent array substrate 108. Continued movement of the substrate 108 toward the microfluidic device 102 then causes the deflection of the longer capillary 150 until the sleeve 1702 on the shorter sampling elements (e.g. 106) contacts the surface of the array substrate 108 (FIG. 17D). Once that occurs, the sleeves ensure that the open end 106a and 150a of each sampling element (106 and 150) is the same distance from the array surface, thus ensuring consistent sampling of materials from the array substrate surface.

The amount of offset for a sleeve structure can vary depending upon the needs of the particular application. In some case that offset can be relatively small, e.g., 10 to 100 µm, whereas other applications can have a larger offset, e.g., 100 µm to 1 mm or more.

The present invention is further illustrated with reference to the following non-limiting examples.

EXAMPLES

Example 1

Reconstituting and Sampling of Nucleic Acids System Set-Up and Operation

Figure 9A:
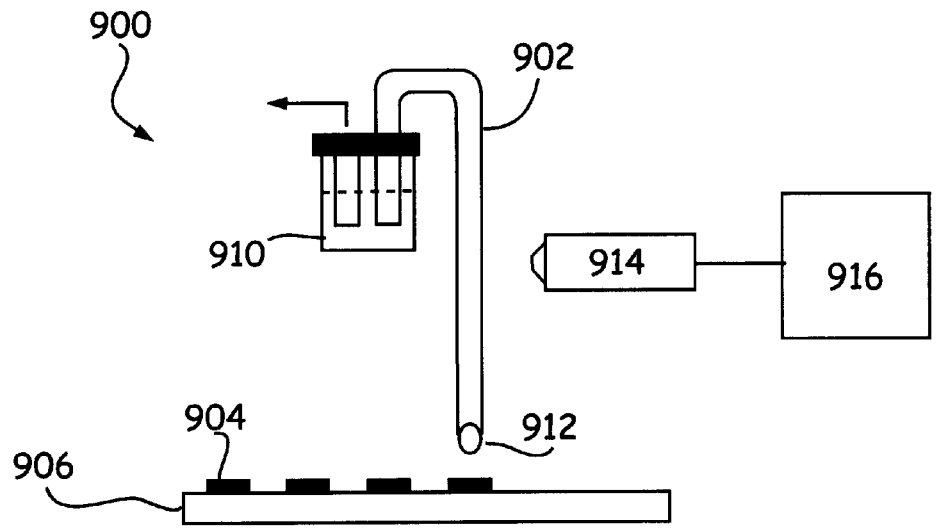
FIGS. 9A and 9B illustrate two model systems used to demonstrate the efficacy of certain aspects of the systems of the present invention.
Figure 9B:
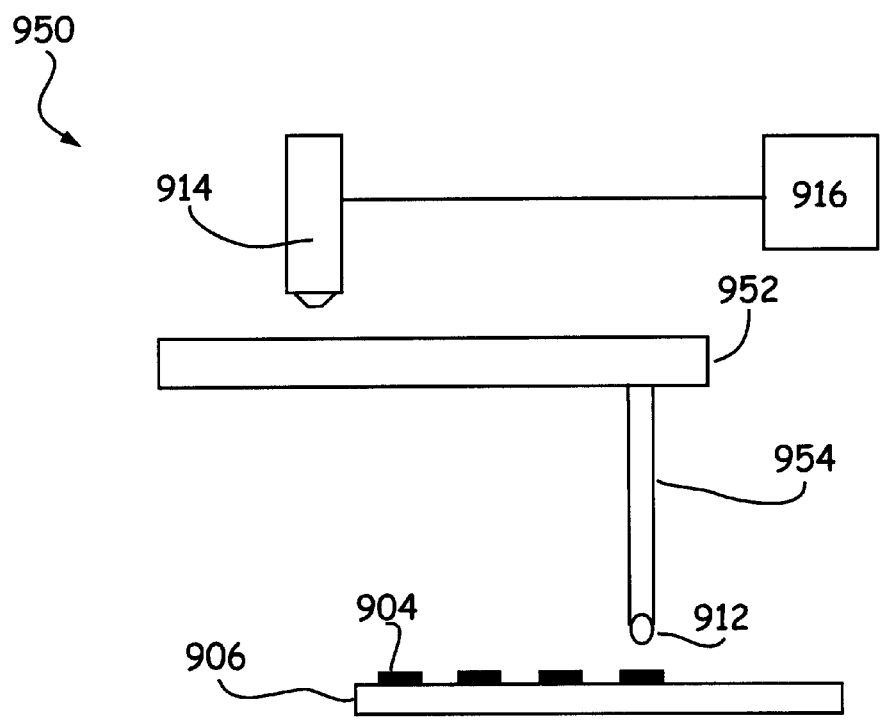

Two different system set-ups were used to demonstrate the sampling and analysis systems of the present invention. These are illustrated in FIGS. 9A and 9B. FIG. 9A shows a system 900 that uses a single capillary 902 to dissolve and aspirate the dried reagents 904 from the surface of a substrate 906. The system included a library substrate holder (not shown) that fixed the polymeric substrate card 906 between two pieces of aluminum. The aluminum holder was then attached to a robot arm, which allowed the card to move in three dimensions (+/−0.5 µm resolution). The capillary 902 was fixed above the card 906 and fed into a waste well 910. Vacuum and pressure (indicated by the arrow) were applied through the waste well using a syringe pump (not shown), to expel a buffer droplet 912 from the capillary tip and sip up rehydrated compound 904 from the surface of the card 906. For detection purposes, a small window was burned in the capillary polyimide coating. An optical system 914 consisting of an arc lamp, PMT and 30× objective, was then focused through the window so that rhodamine labeled molecules could be detected. The measured signal from the PMT was transmitted to a computer 916 for recording and documentation of the experiment.

The second system 950 shown in FIG. 9B, utilized the same substrate configuration. The capillary, however, was replaced by an NS71 sipper chip 952 (shown in FIG. 9C and substantially similar to the chip shown in FIGS. 1 and 2), which includes an integrated capillary element 954 in communication with channels in the interior portion of the device 952 (the point of communication between the external capillary and the internal channels is shown from the top view as a black spot in FIG. 9C). The syringe pump (not shown) was attached to the waste port on the chip and controlled both pressure and vacuum (as shown by the arrow). The detection system 912 was also the same but was re-oriented to detect the fluorescent signal of molecules flowing through the central channel of the chip 952.

All reagent deposition were achieved using the single capillary setup shown in FIG. 9A. Once the capillary and substrate were in place, the computer was programmed to move the substrate relative to the capillary, and expel a certain volume of fluid from the capillary in order to generate a desired pattern of material spots on the surface of the substrate, e.g., number and spacing of spots. Typical numbers were 2000 µm center to center spot spacing and +/−2.0 psig through an 8 inch, 50 µm I.D. glass capillary. The capillary was usually about 50 µm from the card surface during deposition. Once the appropriate data was entered and the program was initiated, the robot moved the substrate card holder so that the capillary was in the reagent well. The reagent was pulled into the capillary for 15 seconds, after which, the substrates card holder moved so that the capillary was positioned over the first spot. Pressure was then applied to the capillary for 13 seconds so that a drop of reagent was formed on the card. After 13 seconds, the substrate card holder moved back to the reagent well to pull up the material for the second spot. This was repeated as necessary.

To dissolve and aspirate the dried reagents, the single capillary and the sipper chip method (FIGS. 9A and 9B) were both used. Regardless of the method, the setup was essentially the same. The program was told the location of the buffer well, the first spot location, the spot spacing and the pressure/vacuum necessary to rehydrate and aspirate the dried material. Where the capillary method was used, the spot location was known from the deposition process. The method of redissolving the reagent was then done one of two ways. In the first case, a positive pressure method was used where the syringe pump pulled up buffer for 25 seconds at −2.0 psig and then dispensed a small amount of that buffer at the reagent spot (2.0 psig for 9 seconds). Once the drop was dispensed, it was pulled back into the capillary (−2.0 psig) for 8 seconds. The robot then moved back to the starting position so that the capillary was in the buffer well. This was repeated for each spot. As the dissolved reagents passed by the capillary window, they were detected by the PMT and displayed by the computer.

The second method of dissolving the compound used a hanging drop from the capillary element. The system was setup the same as the positive pressure method except that no positive pressure was used. The capillary sipped up buffer when in the buffer well for 12 seconds at −2.0 psig. The pressure then changed to 0 psig and the capillary moved to the reagent spot. As the capillary left the buffer well, a hemispherical drop of reagent remained suspended from the capillary end. The radius of the drop matches the radius of the capillary and is approximately 13 nl in volume. When the drop touched the reagent spot, the reagent dissolved. The system waited for three seconds while the reagent dissolved in the drop before aspirating the drop into the capillary at −0.5 psig for 5 seconds.

When using a sipper chip to dissolve the reagents, the process was very similar to using a capillary. However, in order to avoid backflow along any of the side channels of the sipper chip, it was desirable to avoid applying a positive pressure to the waste well of the chip. As such, the hanging drop method was found to be most suitable with these chips. The back-flow problem could also be addressed using control of pressure at the various ports/reservoirs of the device. It was also noted that the system performed optimally when the pressure was kept constant for the duration of the assay, e.g., −0.5 psig. During sipper chip setup, the location of the buffer well and first spot on the card were reset as compared to the single capillary system, as the capillary used to deposit the spots was in a different placement from the capillary element integrated into a chip. Typical parameters used with the sipper chip were as follows: constant vacuum of −0.5 psig; buffer dwell time of 90 seconds; sample dwell time of 6 seconds.

Sampling Rhodamine and Rhodamine-labeled DNA

Figure 10:
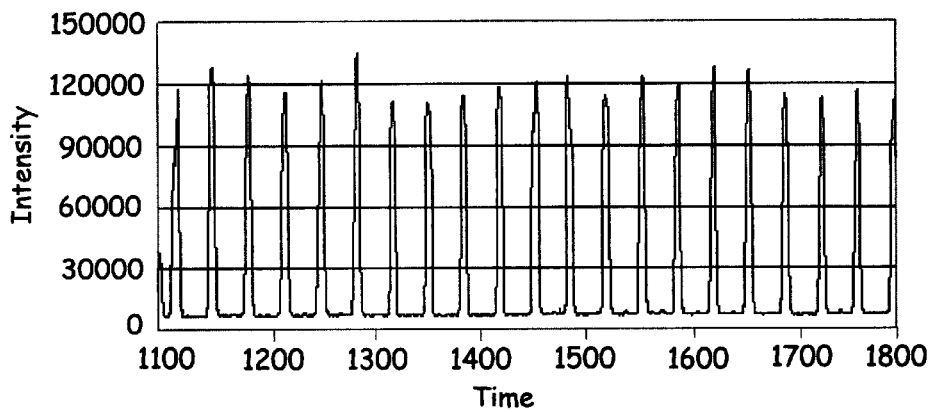
FIG. 10 shows fluorescent intensity changes as rhodamine labeled DNA is sipped from a polypropylene card. Sixty spots were dissolved in total, while 20 peaks are shown in FIG. 10.

Initial tests were performed by simply spotting Rhodamine B/Rhodamine labeled DNA and redissolving it in water. Each of the three methods described above were tested this way. In FIG. 10, Rhodamine labeled DNA was spotted onto polypropylene as outlined above. Sixty spots were retrieved with the data from 20, as shown. A single capillary was used to retrieve the compounds in 50 mM HEPES using a positive pressure method. On average the concentration of material retrieved was at 60 µM. This concentration varied by +/−8% (1 s.d.) between peaks. As shown in FIG. 10, the fluorescent intensity changes as rhodamine labeled DNA is sipped from a polypropylene card.

Figure 11A:
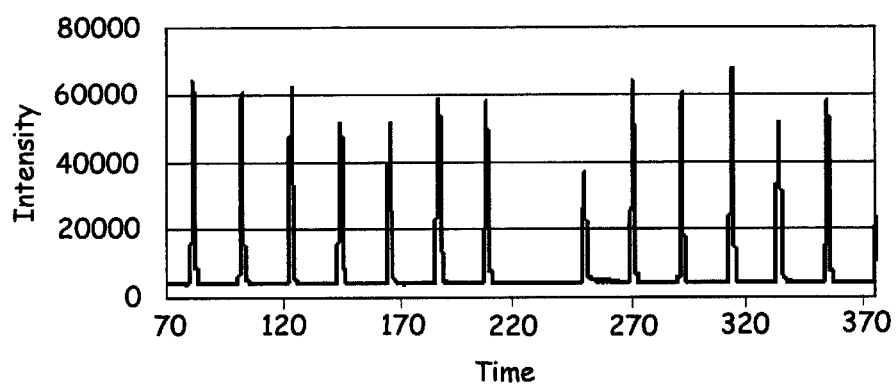
FIGS. 11A and B illustrate resolubilization and sampling of rhodamine labeled DNA from Teflon cards using a single capillary system and a sipper chip system, respectively.
Figure 11B:
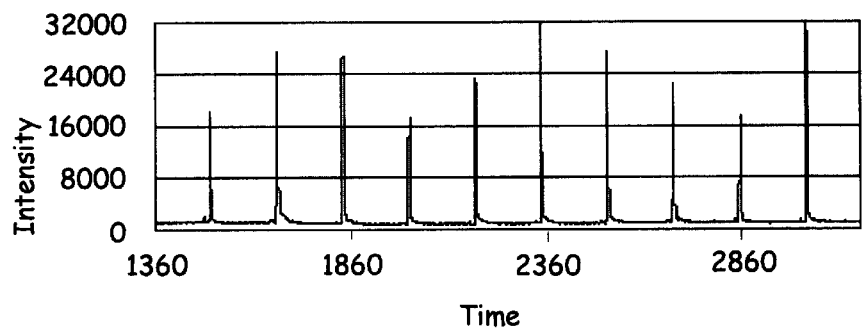

The data in FIGS. 11A and 11B illustrate use of the hanging drop method to dissolve spots of rhodamine labeled DNA on Teflon using both a single capillary set-up (FIG. 11A) and a sipper chip method (FIG. 11B). In FIG. 10, a single fused silica capillary is used. In FIGS. 11A and 11B, a sipper chip was used. As shown in FIG. 11A, peak heights are reproducible to within 20% (1 S.D.) using this particular method. Variability in sampling efficiencies in these plots appears to stem from surface variations in the library substrate surfaces, and static electrical interactions, and is easily remedied by appropriate selection and treatment of the library substrates. As shown in FIG. 11B, Rhodamine labeled DNA was spotted onto Teflon, and the spots were redissolved and aspirated onto an NS71 sipper chip using the method described above.

Example 2

Integrated Sampling and SNP Hybridization Analysis

Hybridization reactions were used to demonstrate an integrated sampling and reaction operation on a chip from dried reagents. Molecular beacons were used as indicators of hybridization. These molecular beacons are DNA molecules where the 5' end has a dabcyl quenching group and the 3' end has a fluorescent moiety. The last five bases on both the 3' and 5' ends are complimentary and thus the DNA strand can wrap around and hybridize to itself. This conformation causes the dabcyl and fluorescent moiety to be sufficiently close that the fluorescence is quenched. The remaining unhybridized region of the DNA molecule is on average 15 to 25 nucleotides in length. When a target DNA molecule, which is complimentary to this region, is in solution, the target will hybridize to the beacon and cause the loop to open. The dabcyl and fluorescent molecule will then be sufficiently far apart that the hybrid will fluoresce. Single nucleotide polymorphisms have been detected using molecular beacons with greater discrimination than that seen using linear DNA molecules (Tyagi et al. Nature Biotechnology, 16, 1998).

Figure 9C:
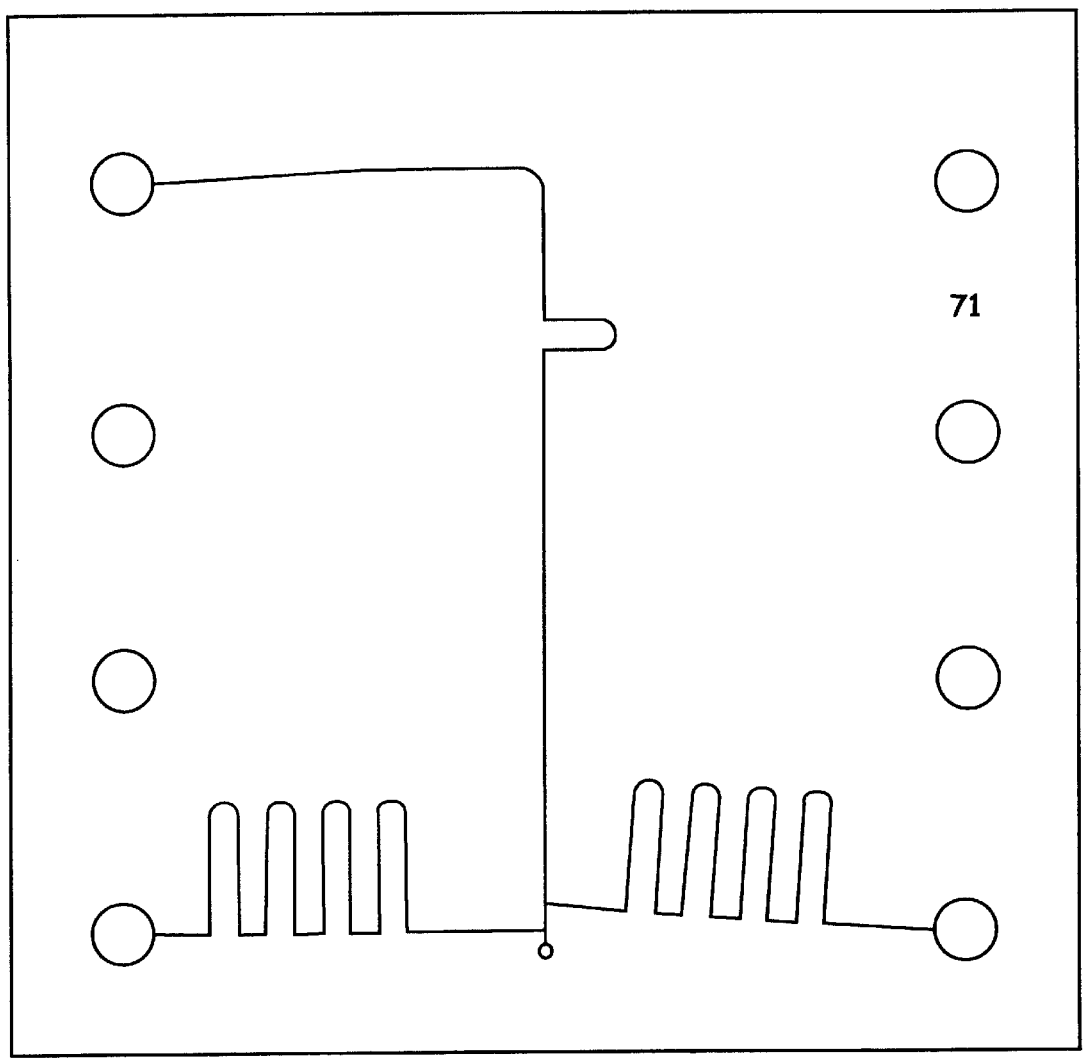
FIG. 9C illustrates the channel layout of an NS71 sipper chip.

In the demonstrating the efficacy of the sampling and reaction system of the invention, the molecular beacon protocol outlined by Tyagi et al. was followed. The beacon sequence was 5' Tamra—gcg aga agt taa gac cta tgc tcg c—dabcyl 3' and the perfect match target sequence was 5'-cat agg tct taa ctt—3'. Three central position mismatch sequences were also used to demonstrate SNP discrimination. Two types of experiments were run. In one case, the targets were spotted onto the card or substrate and in the other the beacon was spotted onto the card or substrate. Before spotting either reagent, the concentrations of reagents needed for the reaction were calculated considering several factors, including the concentration ratio of target to beacon. For purposes of this experiment, a three-fold excess of target to beacon was determined to give reasonable discrimination. Second, the chip design was examined to determine what percentage of each reagent would be present in the reaction channel. The channel geometry or mask layout of the device used is illustrated in FIG. 9C. In the device used, the side arms contribute approximately 30% of the flow down the central channel, whereas the capillary element contributes approximately 70%. Third, because of the spotting and reconstitution methods, the concentration of dissolved material on the card was determined to be approximately 10× the spotting concentration. Once all this was considered, the appropriate concentrations were determined for the reactions. Typical concentrations on the chip were 30 $\mu$M beacon and 100 $\mu$M target. This translates into 100 $\mu$M beacon in the side arm and reagent wells and library substrate spots made with 15 $\mu$M target.

Figure 12:
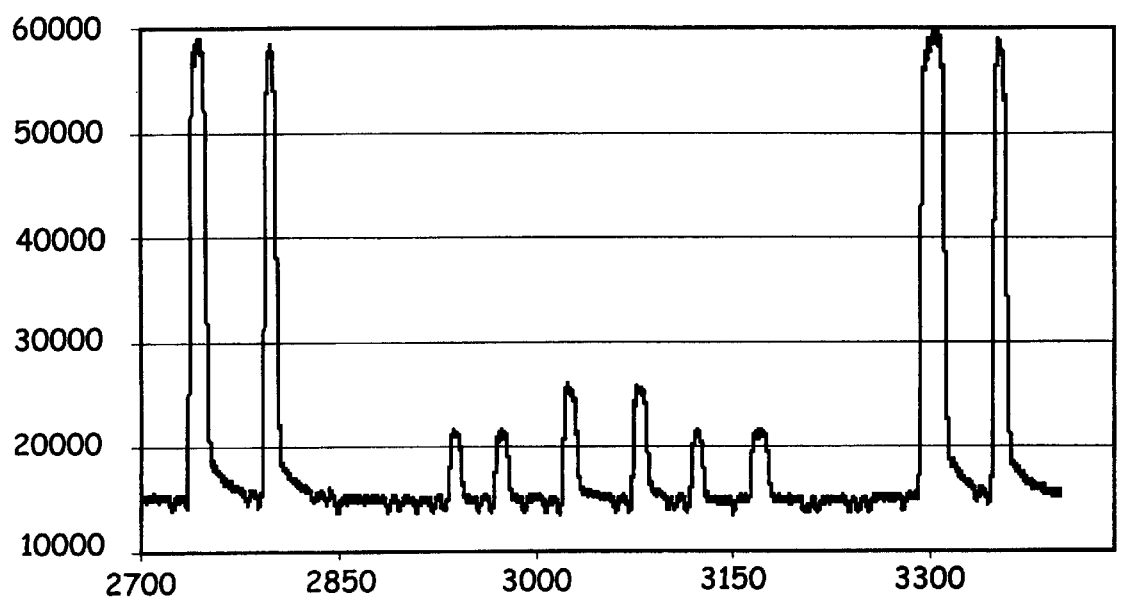
FIG. 12 illustrates discrimination of single base mismatches between the molecular beacon sequence and four liquid oligonucleotide targets in a microfluidic device.

FIG. 12 shows discrimination of the molecular beacon sequence when the beacon is in the side arm wells at 100 $\mu$M and the 4 possible targets (perfect match and three mismatches are all liquid in this assay, not dried) are in the buffer wells at 150 $\mu$M. As indicated by the plot of FIG. 12, SNP discrimination is very clear using this method. Specifically, as shown, the perfect hybrid match and the three possible central position mismatches (150 uM in the buffer well, 100 uM in the reaction channel) are clearly distinguishable. The first (lack of) peaks which are at 2800 seconds represent the 'A' mismatch, the peaks at approximately 2900 seconds represent the 'G' mismatch and the peaks just after 3000 seconds represent the 'T' mismatch.

Figure 13:
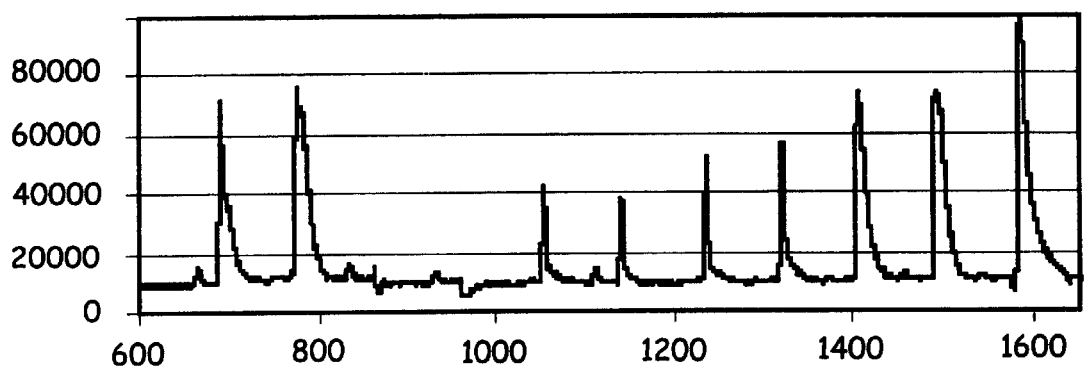
FIG. 13 illustrates discrimination of single base mismatches between the molecular beacon sequence and four dried oligonucleotide targets that were dried onto a solid substrate, where the dried reagents were reconstituted and aspirated into a microfluidic device for the analysis.

FIG. 13 illustrates a similar example to that shown in FIG. 12 except that the sampled materials are dried, rather than in fluid form. Specifically shown is the hybridization of a molecular beacon (concentration in side arm wells at 100 $\mu$M) to the perfect match DNA target and the three possible central position mismatch targets. The three pairs of SNP peaks above correspond to the 'A' mismatch, 'G' mismatch and 'T' mismatch accordingly. The DNA targets were spotted onto the library card at 150 $\mu$M and were therefore approximately 1 mM in the reaction channel. This concentration of target is also readily and routinely adjustable to optimize for maximum discrimination between mismatches. Specifically, as shown, target concentrations were somewhat higher than optimum, to ensure sufficient material was accessed. However, this higher concentration resulted in a reduced level of discrimination between variant sequences.

Figure 14:
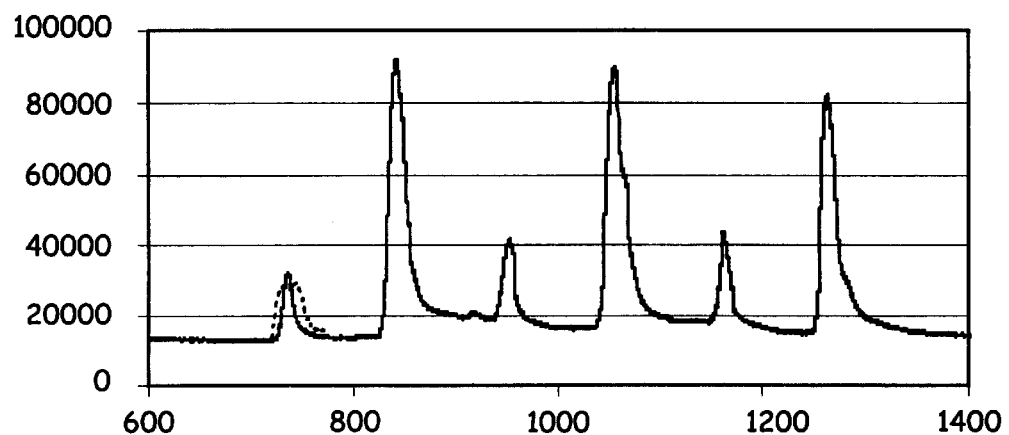
FIG. 14 illustrates discrimination of single base mismatches between an oligonucleotide target sequence and two molecular beacon sequences that were dried onto a surface of a solid support, where the dried reagents were reconstituted and aspirated into a microfluidic device for analysis.

In FIG. 14, the experiment was reversed, such that the two different beacons were spotted onto the card and the target to one beacon was placed in the side arm wells of the chip. The background fluorescence of the unreacted beacon is shown in the plot. The target was deposited into the chip in the side arms at 150 $\mu$M and the beacons were spotted onto the card at 50 $\mu$M. Only one beacon was a perfect match to the target, which is evident from the two different peak heights in the plot of FIG. 14. The two peaks shown at approximately 750 seconds represent control peaks, e.g., a perfect match hybridization and a background fluorescence level of the beacon, alone. The more rounded peak shows the background fluorescence of each sipped unreacted beacon, which is used in order to provide meaningful discrimination in the hybridization assays. The subsequent peaks all show reduced levels of fluorescence, e.g., reduced beacon hybridization, representing lower hybridization efficiencies resulting from the single base mismatches.

Example 3

Electrical Sensing System

Figure 8A:
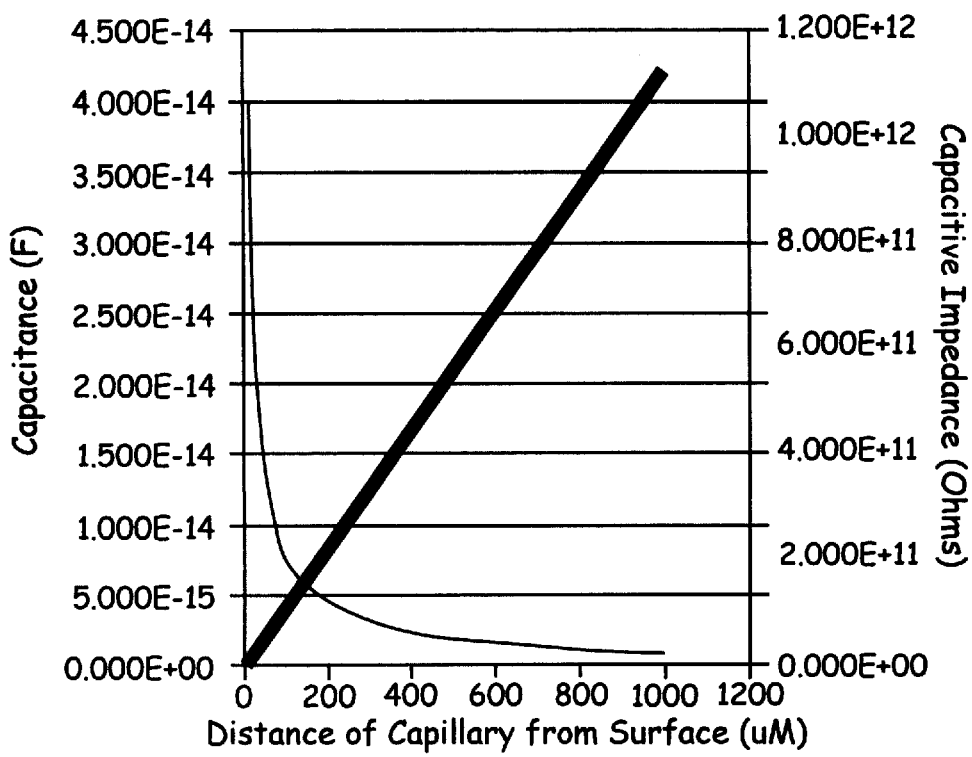
FIGS. 8A, 8B and 8C are plots of capacitance phase vs. distance from the substrate surface for a model capillary system.
Figure 8B:
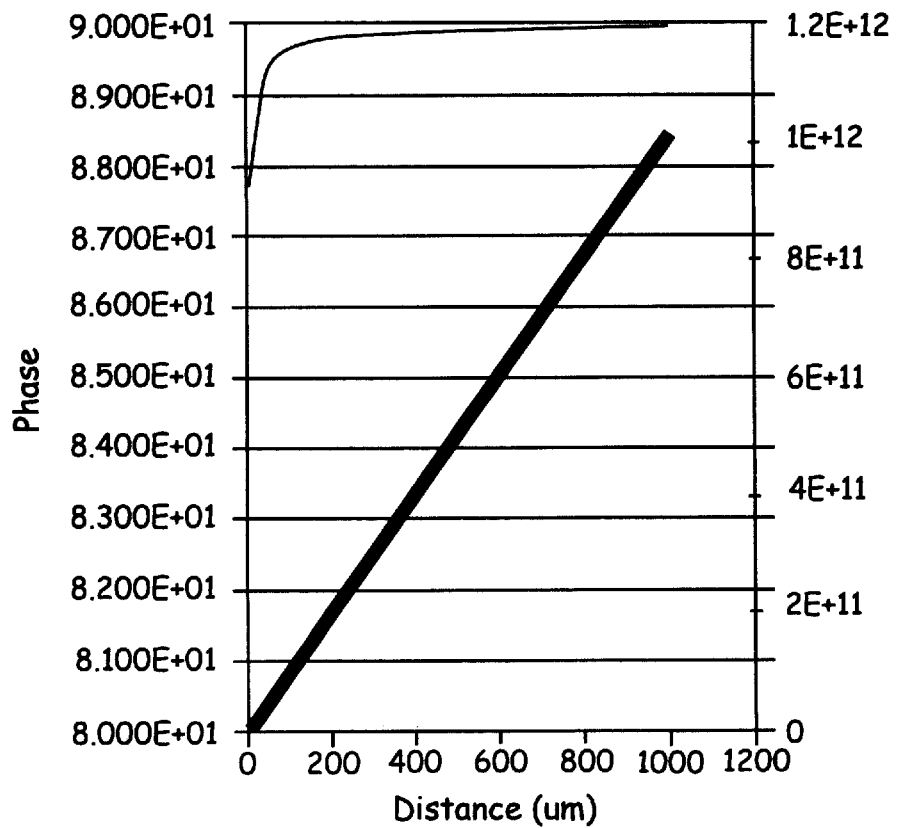
Figure 8C:
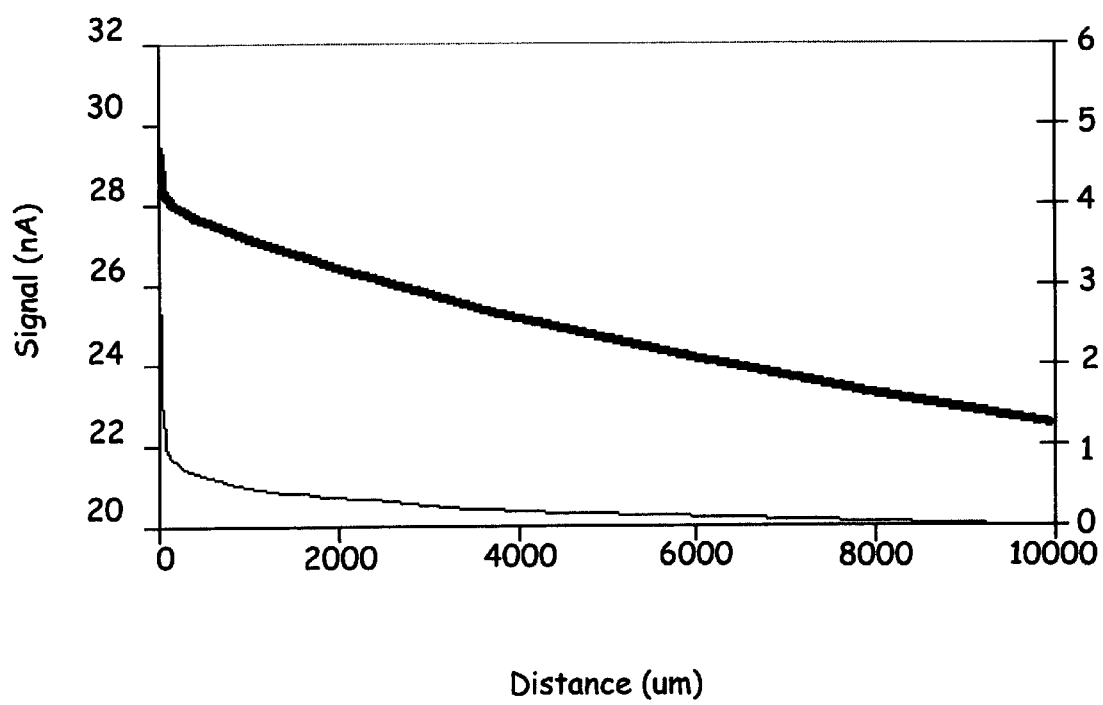

As described above, in at east certain aspects of the instant invention, a sensing system is utilized to facilitate sampling of materials from the library substrate. An electrical sensing system was modeled on treatment of the fluid drop-air gap-substrate as a capacitor. This circuit is illustrated in FIG. 6. When an AC current is applied through the circuit, the phase angle of a simple model system is given by the equation:

$$\theta = \arctan(1/\omega C/R)$$

Where C is capacitance and R is resistance. FIGS. 8A and 8B illustrate theoretical calculations of the phase angle and impedance as a function of the distance for a system having 1 gigaohm of resistance in the capillary and a 1 $\mu$m thick Teflon coating covering a metal plate as the substrate. In FIG. 8A, the thin line represents capacitance for a Teflon® thickness of 1 $\mu$M and the thick line represents capacitive impedance (Ohms) at $10^3$ Hz. In FIG. 8B, the thin line represents phase and the thick line represents resistance. FIG. 8C shows actual impedance measurements made using a model capillary system. The thick line represents the signal and the thin line represents phase. The fluid used was 25 $\mu$M HEPES buffer, and the capillary was 2 cm long with an inner diameter of 20 $\mu$m and an outer diameter of 360 $\mu$m. An aluminum plate overlaid with a 25 $\mu$m thick sheet of Saran® wrap was used to simulate a Teflon® coating.

Figure 15:
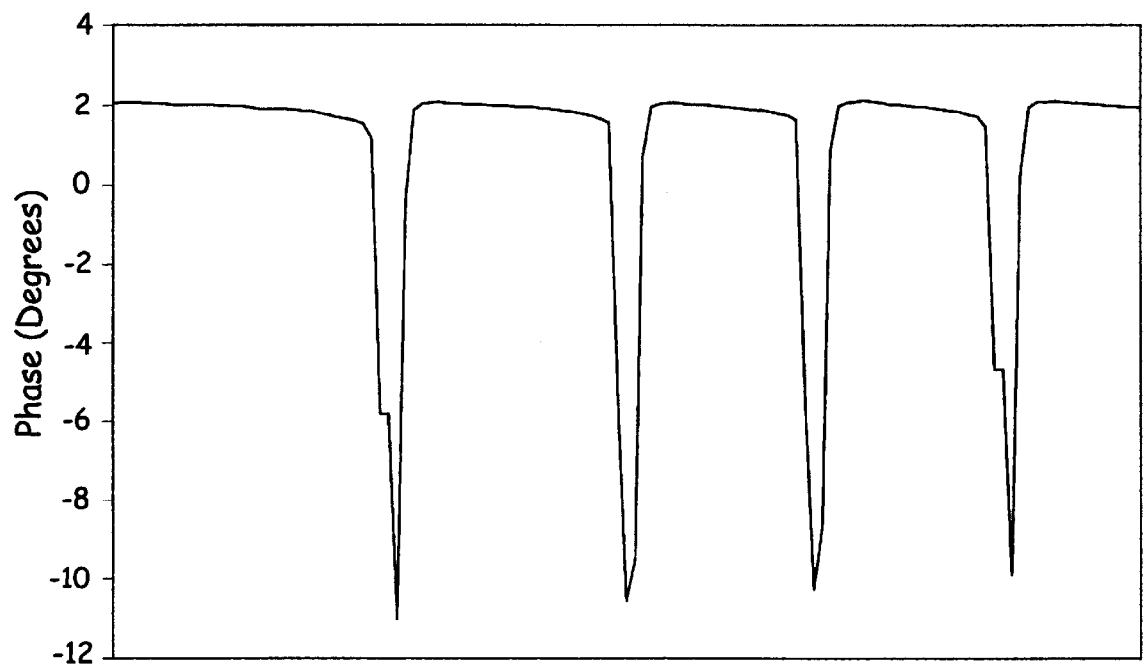
FIG. 15 shows measurements from an electrical sensing system coupled to a microfluidic capillary element and planar solid substrate during a multiple accession run where the capillary element was repeatedly contacted with the surface of the planar solid substrate.

FIG. 15 illustrates a plot of impedance representative of multiple accession events, e.g., where a fluid drop at the end of the capillary is contacted with a metal substrate card, using this electrical sensing method. As can be seen, a number of accession events can be carried out relatively quickly (as shown, intervals are approximately 20 seconds, but could readily be shortened) and accurately using this method.

Example 4

Optical Sensing System

A sampling system was set-up substantially as shown in FIG. 7. A red diode laser (632 nm) was used as the light source 702, and a photodiode was used as the detector 706. The optical train also included the following filters: 1) excitation filter=634 nm; 2) beamsplitter=670 nm; and emission filter=700 nm. The chip was substantially the same as that described in the above examples except that the capillary element was Teflon coated rather than polyimide coated, as polyimide has a relatively high fluorescence level which would contribute to background fluorescence levels.

The library substrate was simulated using a glass microscope slide covered with vinyl tape (Scotch 35 vinyl tape (orange)), which fluoresces brightly at the wavelength of the diode laser. The library substrate was placed upon a standard x-y-z translation stage (Parker) for movement relative to the chip. The objective was placed approximately 1 mm above the upper surface of the chip, giving what appeared to be maximum coupling of the laser into the capillary channel and maximum observed changes in fluorescence levels.

Figure 16:
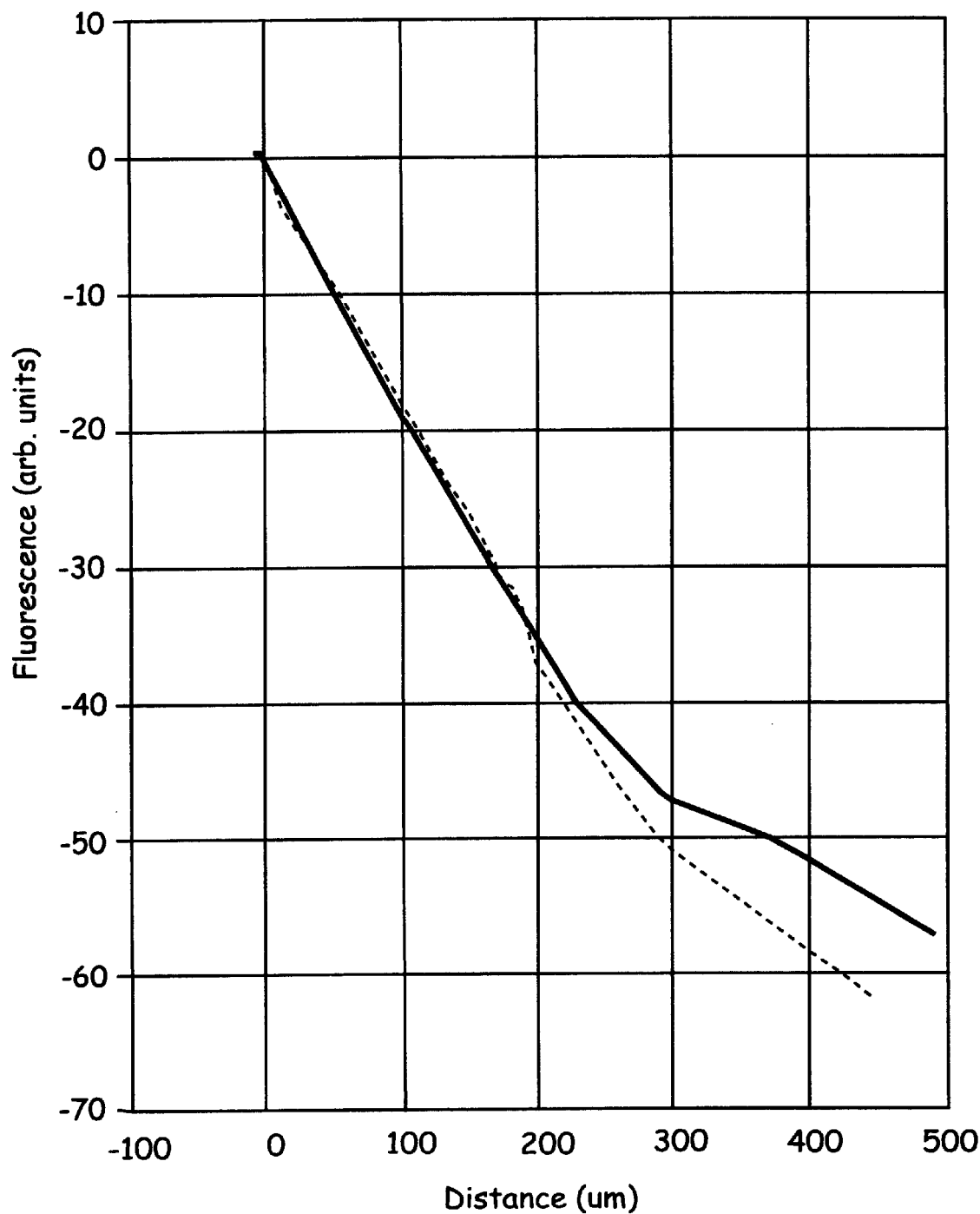
FIG. 16 illustrates sensing data from an optical sensing system of the present invention. Specifically shown is a plot of fluorescence intensity vs. distance between a substrate and capillary, while a library substrate is moved into and out of contact with a capillary element of a microfluidic device.

The experiment was commenced by placing the open end of the capillary element into contact with the surface of the library substrate (as confirmed by magnified visual inspection). The data from the experiment are plotted in FIG. 16. As shown, the fluorescent signal is a reasonably sensitive function of the distance to the surface, with the slope near contact being equal to about 0.2 fluorescence units/$\mu$m. The fluorescence then stayed constant once contact was made with the surface. The plots shown correspond to movement of the capillary toward the substrate (dashed line) and moving away from the substrate (solid line). As can be seen, this method provides a useful method of ascertaining distance of the capillary element from the substrate surface, and/or contact with that surface.

Example 5

Reproducibility of Sampling and Assay Results

The chip based assay system, e.g., as shown in FIG. 9B was employed in monitoring the reproducibility of the overall system in both simple compound sampling and assay performance.

Figure 18:
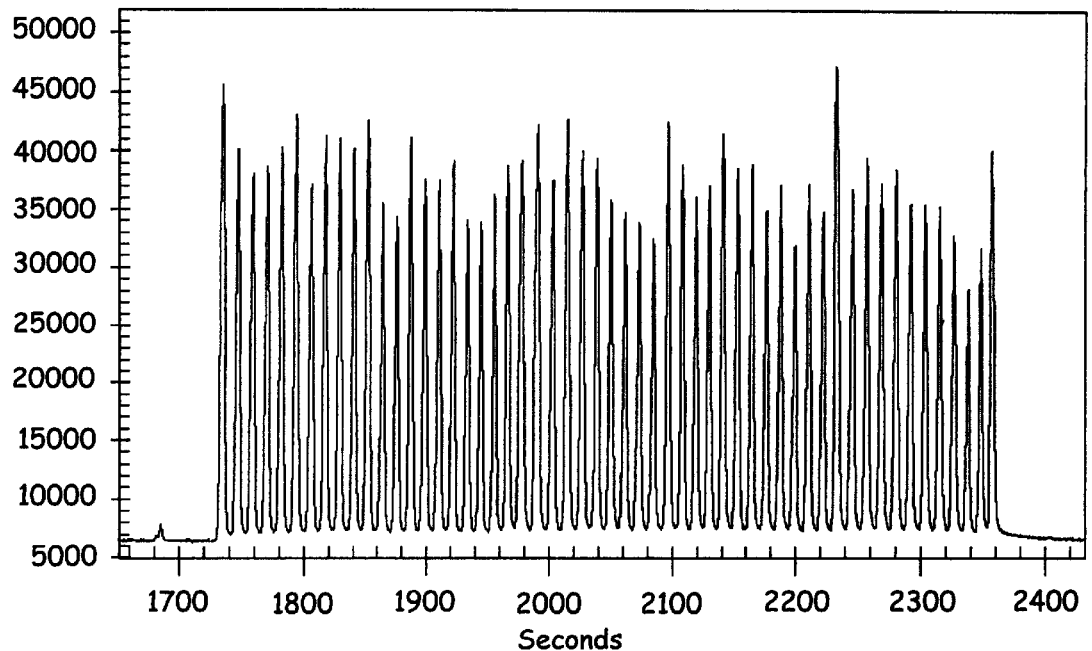
FIG. 18 is a plot of fluorescence vs. time from a channel in a microfluidic device which was used to repeatedly sip dried fluorescent compounds from the surface of a substrate card.

In a first experiment, a fluorescent compound, Edans, was spotted at 100 $\mu$M onto an aminopropyl silanated glass microscope slide, where the spotted solution comprised Edans, DMSO, PEG (10 Kd M.W. at 1%) and dextran (65 Kd at 0.1%). Approximately 5 nl spots were deposited in a standard grid format, and evaporatively dried. The sampling capillary of the chip was aligned using the four corner optical alignment method described herein. Following alignment, more than 50 spots were visited, redissolved by a buffer drop from the sampling capillary, and drawn into the channel network in the interior of the chip. The fluorescent signal from each sampled spot, as it passed through the main channel of the chip, is shown in FIG. 18. As can be seen, fluorescent intensity for each spot is highly regular and always detectable. The average background-subtracted intensity was approximately 29,000 counts with a CV of 12%.

Figure 19:
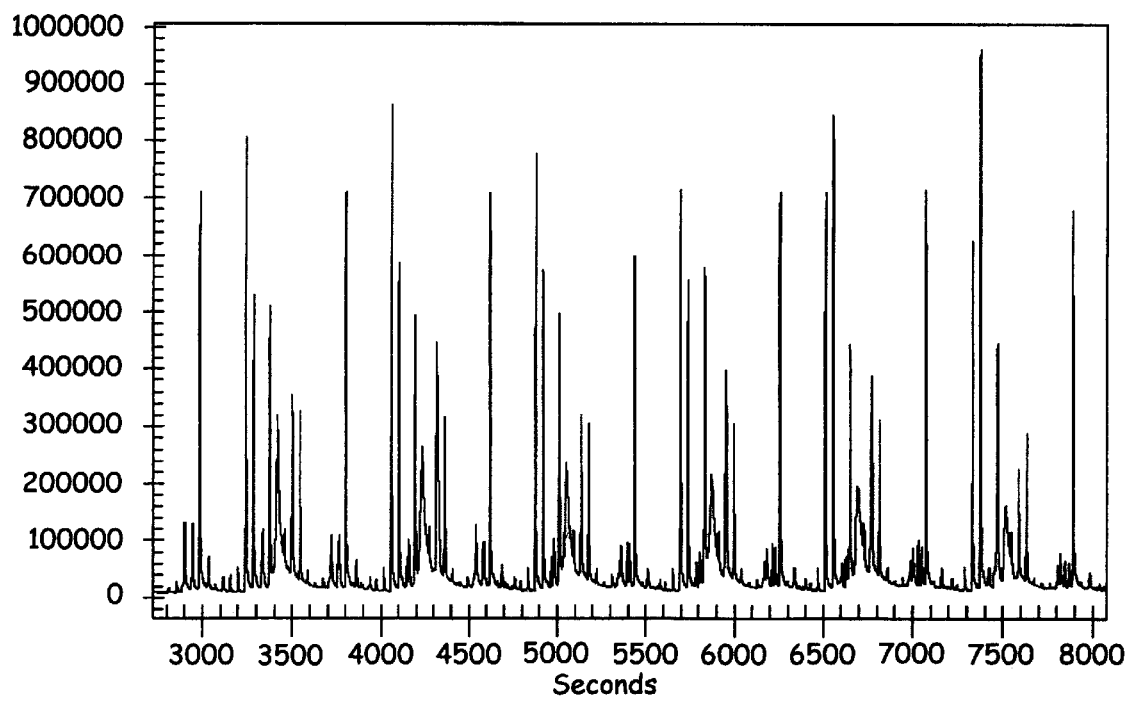
FIG. 19 is a plot of fluorescence vs. time for repeatedly sipping multiple different dried fluorescent compounds from the surface of a substrate card.

A second experiment employed a different spotting solution and different set of compounds from the first. Specifically, 19 fluorescent compound library compounds were separately spotted onto an aminopropyl silanated glass slide as described above, where the spotting solution, in addition to the individual compound, also included DMSO, dextran (65 Kd MW, 1%) and dextran sulfate (500 Kd MW, 0.1%). The compounds were then sipped in 20 separate runs, e.g., all 19 compounds were sipped in 20 sets. FIG. 19 illustrates the fluorescent intensity data from a portion of the overall screen. As can be seen, from set to set, the 19 different compounds gave similar results. The background-subtracted peak heights were determined and analyzed to determine a standard deviation for each compound. For less fluorescent compounds, CVs were relatively high, due to the lower fluorescent intensity, whereas higher fluorescence compounds had CVs that were substantially lower. In general, the CVs ranged from approximately 6 to 41%, with the average being approximately 20%.

Figure 20:
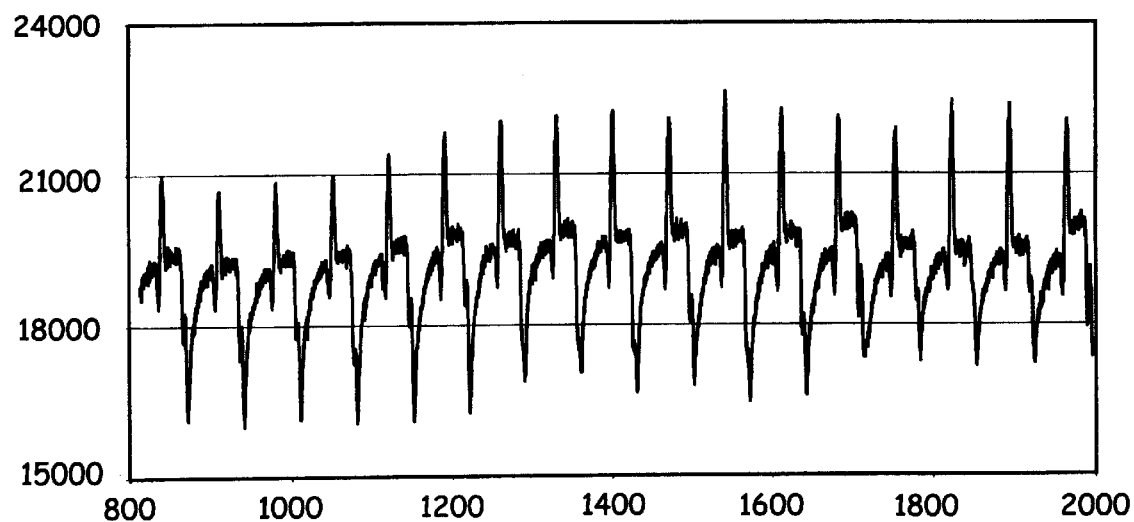
FIG. 20 is a plot of fluorescence vs. time for a continuous flow HSA binding assay, where fluorescence level is indicative of the amount of a fluorescent dye bound to HSA, and reductions in fluorescence are indicative of displacement of that dye.

A third experiment combined sampling with an assay application within the chip. In particular, the chip was used to run a human serum albumin (HSA) binding assay in continuous flow mode, while different compounds were sipped into the device and their ability to bind HSA (as measured by displacement of a fluorescent dye from HSA) was determined. Three different compounds with known binding activity to HSA were spotted repeatedly onto a Teflon® substrate as described above, and dried. The different compounds were then sipped by aspirating 1× PBS onto the compounds from the sampling capillary and drawing the compound into the chip. In the main channel of the chip, HSA was continually mixed with a fluorogenic HSA binding dye (dansylsarcosine) whereupon the compounds bind, and the mixture was flowed along the main channel past a detector. Displacement of the dye results in a reduction in the amount of fluorescence emitted by the dye. FIG. 20 shows the fluorescent signal of the HSA/dye mixture with the periodic introduction of the different HSA binding compounds that were sipped into the main channel. As can be seen, each different compound gave a highly reproducible fluorescent dip with each spot sipped.

Figure 21:
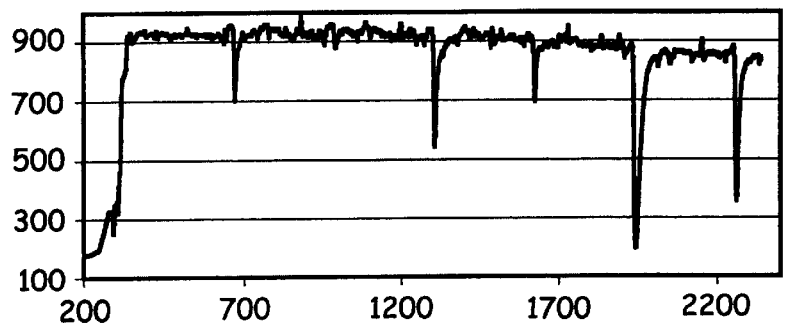
FIG. 21 illustrates a TCPTP enzymatic reaction using the sample substrate array as a source of inhibitors.

The efficacy of the systems of the invention with respect to enzyme assays is further illustrated in FIG. 21 illustrates a data plot of a T-cell protein tyrosine phosphatase (TCPTP) when screened against three known inhibitors that were provided dried on a solid substrate along with negative control compounds. Each inhibitor was spotted at two different concentrations (100 and 25 $\mu$M) in DMSO with 1% Dextran (65 kD MW) as an excipient. Using the assay formats and microfluidic devices (NS-71) described above, the various spotted compounds were hydrated from the capillary tip and drawn into the microfluidic device where they were combined with the assay components (enzyme and substrate (DiFMUP). Approximately 25% of each compound spot was dissolved in each sampling with the same approximate volume of hydrating fluid as deposition fluid, implying an approximate concentration of 25 $\mu$M and 6 $\mu$M for the higher and lower concentration spots, respectively. At these approximate concentrations, the inhibitory response as shown in FIG. 21 is comparable to that seen in purely liquid formats, e.g., samples from a multiwell plate.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method of sampling compounds into a microfluidic channel, comprising:

providing a plurality of different compounds reversibly immobilized on a first surface of a substrate;

providing a capillary element having a microfluidic channel disposed therethrough, the capillary element having at least one open end, and a volume of solubilizing fluid present at the open end of the capillary element;

moving the solubilizing fluid at the open end of the capillary element into contact with a first compound on the surface of the substrate;

sensing when the solubilizing fluid contacts the surface of the substrate, the solubilizing fluid dissolving at least a portion of the first compound; and drawing at least a portion of the dissolved first compound into the capillary element.

2. The method of claim 1, wherein the step of providing the plurality of different compounds reversibly immobilized on a first surface of a substrate comprises providing the plurality of different compounds dried onto the first surface of the substrate.

3. The method of claim 1, wherein the volume of solubilizing fluid at the open end of the capillary element comprises a retained drop at the open end of the capillary element.

4. The method of claim 3, wherein the moving step comprises moving at least one of the substrate or the capillary element to place the retained drop into contact with the first compound on the first surface of the substrate.

5. The method of claim 4, wherein the moving step comprises moving the substrate relative to the capillary element to place the fluid into contact with the first compound.

6. The method of claim 1, wherein the volume of fluid at the open end of the capillary element is expelled from the microfluidic channel disposed within the capillary element.

7. The method of claim 6, wherein the moving step comprises:
moving the capillary element to a position adjacent to the first compound, and
expelling a volume of the solubilizing fluid from the microfluidic channel disposed within the capillary element to contact the first compound.

8. The method of claim 1, wherein the sensing step comprises sensing an electrical signal that is indicative of contact between the solubilizing fluid and the surface of the substrate.

9. The method of claim 1, wherein the sensing step comprises sensing an electrical signal that is indicative of a distance between the solubilizing fluid and the surface of the substrate.

10. The method of claim 8, wherein the step of sensing an electrical signal comprises detecting completion of an electrical circuit between the fluid at the end of the capillary element and the substrate surface.

11. The method of claim 10, wherein the capillary element is filled with fluid, and the completion of the electrical circuit comprises providing an electrical current through the fluid filled capillary element and detecting completion of the electrical circuit between the capillary element and the substrate.

12. The method of claim 8, wherein the step of sensing an electrical signal indicative of contact between the fluid and the surface of the substrate comprises detecting a change in a level of capacitance between the fluid and the surface of the substrate, which change occurs when the fluid is sufficiently proximal to or contacting the surface of the substrate.

13. The method of claim 12, wherein the step of detecting a change in a level of capacitance comprises detecting a change in phase of an electrical current with respect to an applied voltage between the fluid and the surface of the substrate when the fluid is brought into sufficient proximity or contact with the surface of the substrate.

14. The method of claim 12, wherein the change in phase is measured relative to a reference signal.

15. The method of claim 1, wherein the sensing step comprises optically detecting contact between the fluid and the surface of the substrate.

16. The method of claim 15, wherein the optically detecting step comprises detecting a sufficient change in fluorescence emitted from the surface of the substrate.

17. The method of claim 15, wherein the optically detecting step comprises imaging at least one of the surface of the substrate and the open end of the capillary element, and determining when the solubilizing fluid contacts the surface of the substrate.

18. The method of claim 17, wherein the substrate is transparent, and step of imaging one of the surface of the substrate or the open end of the capillary element comprises directing an imaging system at the surface of the substrate or capillary element from beneath the substrate, relative to the capillary element.

19. The method of claim 17, wherein the step of imaging one of the surface of the substrate and the capillary element comprises directing an imaging system at at least one of the substrate surface and capillary element from a side.

20. The method of claim 1, further comprising repeating the moving, sensing and drawing steps with at least a second compound on the surface of the substrate.

21. The method of claim 1, further comprising repeating the moving, sensing and drawing steps with at least 10 different compounds separately reversibly immobilized on the substrate surface.

22. The method of claim 1, further comprising repeating the moving, sensing and drawing steps with at least 100 different compounds separately reversibly immobilized on the substrate surface.

23. The method of claim 1, further comprising repeating the moving, sensing and drawing steps with at least 1000 different compounds separately reversibly immobilized on the substrate surface.

24. The method of claim 1, further comprising repeating the moving, sensing and drawing steps with at least 10,000 different compounds separately reversibly immobilized on the substrate surface.

25. The method of claim 1, further comprising repeating the moving, sensing and drawing steps with at least 100,000 different compounds separately reversibly immobilized on the substrate surface.

26. The method of claim 1, further comprising repeating the moving, sensing and drawing steps with the first compound.

27. The method of claim 1, further comprising repeating the moving, sensing and drawing steps with the first compound from 1 to 10 times.

28. A method of sampling a plurality of different compounds into a microfluidic channel, comprising:
providing a sample substrate having at least a first surface, the substrate comprising a plurality of different compounds immobilized in a gridded array of one or more rows of different compounds, the different compounds being substantially uniformly spaced within the one or more rows whereby each compound is in a separate discrete region of the first surface of the substrate, the plurality of different compounds being present at a density of a least about 10 different compounds/cm$^2$ of substrate surface;
determining an approximate location of a plurality of the different compounds in the separate discrete regions of the first surface of the substrate which comprises locating at least first and second compound locations on the first surface of the substrate and interpolating an approximate location for substantially all of the different compounds between the first and second compound locations;
separately solubilizing a first compound on the surface;
drawing a portion of the solubilized first compound into a microfluidic channel disposed in a capillary element; and
repeating the solubilizing and drawing steps with at least a second compound on the first surface of the substrate.

29. The method of claim 28, wherein the first and second compound locations have known positions relative to other compound locations on the first surface of the substrate.

30. The method of claim 28, wherein the gridded array of compounds comprises at least two rows of different compounds immobilized on the first surface of the substrate, and the step of determining an approximate location of a plurality of different compounds on the first surface of the substrate further comprises locating first, second and third different compound locations on the first surface of the substrate, wherein the first, second and third compound locations comprise three corner compound locations of the gridded array of different compounds on the first surface of the substrate.

31. The method of claim 28, wherein the plurality of different compounds are present at a density of at least about 100 different compounds/cm$^2$ of substrate surface.

32. The method of claim 28, wherein the plurality of different compounds are present at a density of at least about 500 different compounds/cm$^2$ of substrate surface.

33. The method of claim 28, wherein the plurality of different compounds are present at a density of at least about 1000 different compounds/cm$^2$ of substrate surface.

34. The method of claim 28, wherein the first surface of the substrate a surface area of at least 1 cm$^2$.

35. The method of claim 34, wherein the surface of the substrate comprises at least 100 different compounds reversibly immobilized thereon in discrete regions.

36. The method of claim 34, wherein the surface of the substrate comprises at least 1000 different compounds reversibly immobilized thereon in discrete regions.

37. The method of claim 28, wherein the first surface of the substrate has a surface area of at least 2 cm$^2$.

38. The method of claim 37, wherein the surface of the substrate comprises at least 200 different compounds reversibly immobilized thereon in discrete regions.

39. The method of claim 28, wherein the first surface of the substrate has a surface area of at least 10 cm$^2$.

40. The method of claim 39, wherein the first surface of the substrate comprises at least 1000 different compounds reversibly immobilized thereon in discrete regions.

41. The method of claim 28, wherein the first surface of the substrate has a surface area of at least 20 cm$^2$.

42. The method of claim 41, wherein the surface of the substrate comprises at least 2000 different compounds reversibly immobilized thereon in discrete regions.

43. The method of claim 28, wherein the first surface of the substrate has a surface area of at least 100 cm$^2$.

44. The method of claim 43, wherein the surface of the substrate comprises at least 10,000 different compounds reversibly immobilized thereon in discrete regions.

45. The method of claim 43, wherein the surface of the substrate comprises about 100,000 different compounds reversibly immobilized thereon in discrete regions.

46. The method of claim 28, wherein the surface first of the substrate comprises a metal.

47. The method of claim 46, wherein the substrate comprises glass or quartz.

48. The method of claim 28, wherein the first surface of the substrate is nonconductive.

49. The method of claim 48, wherein the surface of the substrate is selected from a metal oxide, $SiO_2$, $Si_3N_4$, siliconoxynitride and a polymeric material.

50. The method of claim 49, wherein the surface of the substrate is a polymeric material.

51. The method of claim 50, wherein the polymeric material is selected from nitrocellulose, acrylic, polystyrene, parylene, polyvinylidine difluoride (PVDF), polysulfone, polyvinyl chloride, spun polypropylene, polytetrafluoroethylene (PTFE), and polycarbonate.

* * * * *

UNITED STATES PATENT AND TRADEMARK OFFICE
CERTIFICATE OF CORRECTION

PATENT NO.     : 6,620,625 B2
DATED          : September 16, 2003
INVENTOR(S)    : Wolk et al.

It is certified that error appears in the above-identified patent and that said Letters Patent is hereby corrected as shown below:

<u>Column 31,</u>
Line 8, after "substrate", please insert -- has --.

<u>Column 32,</u>
Line 10, please delete "surface first" and insert -- first surface --.

Signed and Sealed this

Eleventh Day of November, 2003

JAMES E. ROGAN
*Director of the United States Patent and Trademark Office*